United States Patent
Annoni et al.

(10) Patent No.: US 12,226,225 B2
(45) Date of Patent: *Feb. 18, 2025

(54) PATIENT-SPECIFIC CALIBRATION OF PAIN QUANTIFICATION

(71) Applicant: Boston Scientific Neuromodulation Corporation, Valencia, CA (US)

(72) Inventors: Elizabeth Mary Annoni, White Bear Lake, MN (US); Jianwen Gu, Valencia, CA (US); Pramodsingh Hirasingh Thakur, Woodbury, MN (US); Bryan Allen Clark, Forest Lake, MN (US); Kyle Harish Srivastava, Saint Paul, MN (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 441 days.

This patent is subject to a terminal disclaimer.

(21) Appl. No.: 17/385,665

(22) Filed: Jul. 26, 2021

(65) Prior Publication Data

US 2021/0345950 A1    Nov. 11, 2021

Related U.S. Application Data

(63) Continuation of application No. 15/867,772, filed on Jan. 11, 2018, now Pat. No. 11,089,997.
(Continued)

(51) Int. Cl.
*A61N 1/36* (2006.01)
*A61B 5/00* (2006.01)
(Continued)

(52) U.S. Cl.
CPC .......... *A61B 5/4824* (2013.01); *A61B 5/4836* (2013.01); *A61B 5/4884* (2013.01);
(Continued)

(58) Field of Classification Search
CPC ................. A61N 1/36071; A61N 1/0456
See application file for complete search history.

(56) References Cited

U.S. PATENT DOCUMENTS

| | | |
|---|---|---|
| 4,297,685 A | 10/1981 | Brainard, II |
| 5,187,675 A | 2/1993 | Dent et al. |

(Continued)

FOREIGN PATENT DOCUMENTS

| | | |
|---|---|---|
| AU | 2017335497 | 4/2020 |
| AU | 2017334841 | 7/2020 |

(Continued)

OTHER PUBLICATIONS

"2015 Sleep in America® Poll Sleep and Pain—Summary of Findings", National Sleep Foundation, (2015), 1-54.
(Continued)

*Primary Examiner* — Alyssa M Alter
(74) *Attorney, Agent, or Firm* — Schwegman Lundberg & Woessner, P.A.

(57) ABSTRACT

This document discusses, among other things, systems and methods for managing pain in a patient. A system may include sensors to sense physiological or functional signals, and a pain analyzer that generates a pain score using the sensed physiological or functional signals and a fusion model. The system includes a calibration module that calibrates the fusion model based on measurements from the sensed physiological or functional signals and a reference pain quantification corresponding to multiple pain intensities. A pain score may be generated using the calibrated fusion model. The system can additionally include a neurostimulator that controls the delivery of pain therapy by adjusting one or more stimulation parameters based on the pain score.

20 Claims, 6 Drawing Sheets

Related U.S. Application Data

(60) Provisional application No. 62/445,095, filed on Jan. 11, 2017.

(51) Int. Cl.
*A61N 1/05* (2006.01)
*A61N 1/372* (2006.01)

(52) U.S. Cl.
CPC .......... *A61B 5/7246* (2013.01); *A61N 1/0534* (2013.01); *A61N 1/0551* (2013.01); *A61N 1/36062* (2017.08); *A61N 1/36071* (2013.01); *A61N 1/36139* (2013.01); *A61N 1/37211* (2013.01); *A61N 1/37247* (2013.01); *A61N 1/37264* (2013.01); *A61B 2560/0223* (2013.01)

(56) References Cited

U.S. PATENT DOCUMENTS

| | | | |
|---|---|---|---|
| 5,774,591 A | 6/1998 | Black et al. | |
| 6,016,103 A | 1/2000 | Leavitt | |
| 6,076,011 A | 6/2000 | Hoover | |
| 6,088,040 A | 7/2000 | Oda et al. | |
| 6,173,260 B1 | 1/2001 | Slaney | |
| 6,480,734 B1 | 11/2002 | Zhang et al. | |
| 6,497,658 B2 | 12/2002 | Roizen et al. | |
| 6,654,632 B2 | 11/2003 | Lange et al. | |
| 6,659,968 B1 | 12/2003 | McClure | |
| 6,731,984 B2 | 5/2004 | Cho et al. | |
| 6,871,099 B1 | 3/2005 | Whitehurst et al. | |
| 7,001,337 B2 | 2/2006 | Dekker | |
| 7,004,907 B2 | 2/2006 | Banet et al. | |
| 7,177,686 B1 | 2/2007 | Turcott | |
| 7,189,204 B2 | 3/2007 | Ni et al. | |
| 7,222,075 B2 | 5/2007 | Petrushin | |
| 7,299,086 B2 | 11/2007 | McCabe et al. | |
| 7,376,457 B2 | 5/2008 | Ross | |
| 7,407,485 B2 | 8/2008 | Huiku | |
| 7,463,927 B1 | 12/2008 | Chaouat | |
| 7,566,308 B2 | 7/2009 | Stahmann | |
| 7,627,475 B2 | 12/2009 | Petrushin | |
| 7,636,602 B2 | 12/2009 | Baru Fassio et al. | |
| 7,650,184 B2 | 1/2010 | Walter | |
| 7,678,061 B2 | 3/2010 | Lee et al. | |
| 7,775,993 B2 | 8/2010 | Heruth et al. | |
| 7,957,809 B2 | 6/2011 | Bourget et al. | |
| 7,986,991 B2 | 7/2011 | Prichep | |
| 8,019,439 B2 | 9/2011 | Kuzma et al. | |
| 8,055,348 B2 | 11/2011 | Heruth et al. | |
| 8,083,682 B2 | 12/2011 | Dalal et al. | |
| 8,192,376 B2 | 6/2012 | Lovett et al. | |
| 8,209,182 B2 | 6/2012 | Narayanan | |
| 8,290,596 B2 | 10/2012 | Wei et al. | |
| 8,332,038 B2 | 12/2012 | Heruth et al. | |
| 8,398,556 B2 | 3/2013 | Sethi et al. | |
| 8,447,401 B2 | 5/2013 | Miesel et al. | |
| 8,475,370 B2 | 7/2013 | McCombie et al. | |
| 8,529,459 B2 | 9/2013 | Malker et al. | |
| 8,606,356 B2 | 12/2013 | Lee et al. | |
| 8,688,221 B2 | 4/2014 | Miesel | |
| 8,744,587 B2 | 6/2014 | Miesel et al. | |
| 8,805,518 B2 | 8/2014 | King et al. | |
| 9,066,659 B2 | 6/2015 | Thakur et al. | |
| 9,072,870 B2 | 7/2015 | Wu et al. | |
| 9,119,965 B2 | 9/2015 | Xi et al. | |
| 9,314,168 B2 | 4/2016 | Watson et al. | |
| 9,395,792 B1 | 7/2016 | Kahn et al. | |
| 9,517,344 B1* | 12/2016 | Bradley | A61N 1/3787 |
| 10,349,212 B2 | 7/2019 | Tartz et al. | |
| 10,610,688 B2 | 4/2020 | Thakur et al. | |
| 10,631,776 B2 | 4/2020 | Annoni et al. | |
| 10,631,777 B2 | 4/2020 | Clark et al. | |
| 10,667,747 B2 | 6/2020 | Annoni et al. | |
| 10,675,469 B2 | 6/2020 | Annoni et al. | |
| 10,729,905 B2 | 8/2020 | Annoni et al. | |
| 10,750,994 B2* | 8/2020 | Annoni | A61B 5/7475 |
| 10,898,718 B2 | 1/2021 | Srivastava et al. | |
| 10,926,091 B2 | 2/2021 | Srivastava et al. | |
| 10,960,210 B2 | 3/2021 | Srivastava et al. | |
| 11,089,997 B2* | 8/2021 | Annoni | A61N 1/36071 |
| 11,395,625 B2 | 7/2022 | Clark et al. | |
| 11,541,240 B2 | 1/2023 | Annoni et al. | |
| 11,571,577 B2 | 2/2023 | Srivastava et al. | |
| 11,857,794 B2 | 1/2024 | Annoni et al. | |
| 2002/0042563 A1 | 4/2002 | Becerra et al. | |
| 2004/0015091 A1 | 1/2004 | Greenwald et al. | |
| 2005/0010262 A1 | 1/2005 | Sharan et al. | |
| 2005/0209643 A1 | 9/2005 | Heruth et al. | |
| 2007/0167859 A1 | 7/2007 | Finneran et al. | |
| 2007/0213783 A1 | 9/2007 | Pless | |
| 2007/0260285 A1 | 11/2007 | Libbus et al. | |
| 2008/0077192 A1 | 3/2008 | Harry et al. | |
| 2008/0177191 A1 | 7/2008 | Patangay et al. | |
| 2008/0249430 A1 | 10/2008 | John et al. | |
| 2009/0124863 A1 | 5/2009 | Liu et al. | |
| 2009/0192556 A1 | 7/2009 | Wu et al. | |
| 2009/0312663 A1 | 12/2009 | John et al. | |
| 2009/0318986 A1 | 12/2009 | Alo et al. | |
| 2010/0016913 A1 | 1/2010 | Arcot-Krishnamurthy et al. | |
| 2010/0286549 A1 | 11/2010 | John et al. | |
| 2011/0015702 A1 | 1/2011 | Ternes et al. | |
| 2011/0021928 A1 | 1/2011 | Giovangrandi et al. | |
| 2011/0112420 A1 | 5/2011 | Nagata et al. | |
| 2011/0124979 A1 | 5/2011 | Heneghan et al. | |
| 2011/0137134 A1 | 6/2011 | Hemmerling et al. | |
| 2011/0172562 A1 | 7/2011 | Sahasrabudhe et al. | |
| 2011/0224749 A1 | 9/2011 | Ben-David et al. | |
| 2011/0306846 A1 | 12/2011 | Osorio | |
| 2012/0046715 A1 | 2/2012 | Moffitt et al. | |
| 2012/0109012 A1 | 5/2012 | Cinbis | |
| 2012/0123223 A1 | 5/2012 | Freeman et al. | |
| 2012/0150545 A1 | 6/2012 | Simon | |
| 2013/0066394 A1 | 3/2013 | Saab | |
| 2013/0165994 A1 | 6/2013 | Ternes et al. | |
| 2013/0211291 A1 | 8/2013 | Tran | |
| 2013/0268016 A1 | 10/2013 | Xi et al. | |
| 2014/0276188 A1 | 9/2014 | Jardin | |
| 2014/0276549 A1 | 9/2014 | Osorio | |
| 2015/0005842 A1 | 1/2015 | Lee et al. | |
| 2015/0025335 A1 | 1/2015 | Jain et al. | |
| 2015/0289803 A1 | 10/2015 | Wu et al. | |
| 2016/0022203 A1 | 1/2016 | Arnold et al. | |
| 2016/0082265 A1 | 3/2016 | Moffitt et al. | |
| 2016/0129272 A1 | 5/2016 | Hou et al. | |
| 2016/0144194 A1 | 5/2016 | Roothans et al. | |
| 2016/0158551 A1 | 6/2016 | Kent et al. | |
| 2016/0243359 A1 | 8/2016 | Sharma | |
| 2016/0302720 A1 | 10/2016 | John et al. | |
| 2016/0350509 A1 | 12/2016 | Sharma | |
| 2016/0361515 A1 | 12/2016 | Jung et al. | |
| 2016/0374567 A1 | 12/2016 | Breslow et al. | |
| 2017/0128722 A1 | 5/2017 | Perez | |
| 2017/0136264 A1 | 5/2017 | Hyde et al. | |
| 2017/0164876 A1 | 6/2017 | Hyde et al. | |
| 2017/0165485 A1 | 6/2017 | Sullivan et al. | |
| 2018/0078768 A1 | 3/2018 | Thakur et al. | |
| 2018/0085055 A1 | 3/2018 | Annoni et al. | |
| 2018/0085584 A1 | 3/2018 | Thakur et al. | |
| 2018/0110464 A1 | 4/2018 | Annoni et al. | |
| 2018/0126169 A1 | 5/2018 | Hou et al. | |
| 2018/0192941 A1 | 7/2018 | Annoni et al. | |
| 2018/0192942 A1 | 7/2018 | Clark et al. | |
| 2018/0192943 A1 | 7/2018 | Annoni et al. | |
| 2018/0193644 A1 | 7/2018 | Annoni et al. | |
| 2018/0193650 A1 | 7/2018 | Srivastava et al. | |
| 2018/0193651 A1 | 7/2018 | Annoni et al. | |
| 2018/0193652 A1 | 7/2018 | Srivastava et al. | |
| 2018/0229040 A1 | 8/2018 | Srivastava et al. | |
| 2019/0022397 A1 | 1/2019 | Srivastava et al. | |
| 2020/0188673 A1 | 6/2020 | Thakur et al. | |
| 2020/0214623 A1 | 7/2020 | Annoni et al. | |
| 2020/0214624 A1 | 7/2020 | Clark et al. | |
| 2020/0238087 A1 | 7/2020 | Annoni et al. | |
| 2020/0359960 A1 | 11/2020 | Annoni et al. | |

(56) References Cited

U.S. PATENT DOCUMENTS

| | | | |
|---|---|---|---|
| 2021/0060343 | A1 | 3/2021 | Srivastava et al. |
| 2021/0128921 | A1 | 5/2021 | Srivastava et al. |
| 2021/0178164 | A1 | 6/2021 | Srivastava et al. |
| 2021/0345950 | A1 | 11/2021 | Annoni et al. |
| 2023/0103448 | A1 | 4/2023 | Annoni et al. |
| 2023/0120858 | A1 | 4/2023 | Srivastava et al. |

FOREIGN PATENT DOCUMENTS

| | | |
|---|---|---|
| EP | 1059064 A2 | 12/2000 |
| EP | 1897586 | 3/2008 |
| EP | 3519037 | 7/2020 |
| EP | 3568069 | 4/2021 |
| KR | 20050053824 | 6/2005 |
| KR | 1020050053824 A | 6/2005 |
| RU | 2559783 C1 | 8/2015 |
| WO | 2007007058 | 1/2007 |
| WO | WO-2009055127 A1 | 4/2009 |
| WO | WO-2010051406 A1 | 5/2010 |
| WO | WO-2011008747 A2 | 1/2011 |
| WO | WO-2011053607 A1 | 5/2011 |
| WO | WO-2013134479 A1 | 9/2013 |
| WO | 2014151860 | 9/2014 |
| WO | WO-2015060888 A1 | 4/2015 |
| WO | WO-2015128567 | 9/2015 |
| WO | WO-2016025989 A1 | 2/2016 |
| WO | WO-2016077786 A1 | 5/2016 |
| WO | 2018052695 | 3/2018 |
| WO | 2018063637 | 4/2018 |
| WO | 2018063912 | 4/2018 |
| WO | 2018080887 | 5/2018 |
| WO | 2019018206 | 1/2019 |

OTHER PUBLICATIONS

"U.S. Appl. No. 15/867,756, Examiner Interview Summary mailed Aug. 28, 2019", 3 pgs.
"U.S. Appl. No. 15/867,756, Non Final Office Action mailed Jul. 1, 2019", 8 pgs.
"U.S. Appl. No. 15/867,756, Notice of Allowance mailed Dec. 19, 2019", 7 pgs.
"U.S. Appl. No. 15/867,756, Response filed Aug. 29, 2019 to Non Final Office Action mailed Jul. 1, 2019", 11 pgs.
"U.S. Appl. No. 15/867,760, Examiner Interview Summary mailed Aug. 28, 2019", 3 pgs.
"U.S. Appl. No. 15/867,760, Non Final Office Action mailed Jul. 1, 2019", 8 pgs.
"U.S. Appl. No. 15/867,760, Notice of Allowance mailed Dec. 19, 2019", 7 pgs.
"U.S. Appl. No. 15/867,760, Response filed Aug. 29, 2019 to Non-Final Office Action mailed Jul. 1, 2019", 11 pgs.
"U.S. Appl. No. 15/867,767, Non Final Office Action mailed Dec. 17, 2019", 11 pgs.
"U.S. Appl. No. 15/867,767, Notice of Allowance mailed Apr. 6, 2020", 5 pgs.
"U.S. Appl. No. 15/867,767, Response filed Mar. 4, 2020 to Non Final Office Action mailed Dec. 17, 2019", 10 pgs.
"U.S. Appl. No. 15/867,772, Advisory Action mailed Dec. 22, 2020", 3 pgs.
"U.S. Appl. No. 15/867,772, Examiner Interview Summary mailed Apr. 29, 2021", 2 pgs.
"U.S. Appl. No. 15/867,772, Examiner Interview Summary mailed Dec. 11, 2020", 2 pgs.
"U.S. Appl. No. 15/867,772, Final Office Action mailed Oct. 22, 2020", 10 pgs.
"U.S. Appl. No. 15/867,772, Non Final Office Action mailed Apr. 2, 2020", 9 pgs.
"U.S. Appl. No. 15/867,772, Notice of Allowance mailed Apr. 23, 2021", 5 pgs.

"U.S. Appl. No. 15/867,772, PTO Response to Rule 312 Communication mailed Dec. 22, 2020", 4 pgs.
"U.S. Appl. No. 15/867,772, Response filed Jun. 30, 2020 to Non Final Office Action mailed Apr. 2, 2020", 10 pgs.
"U.S. Appl. No. 15/867,772, Response filed Dec. 15, 2020 to Final Office Action mailed Oct. 22, 2020", 12 pgs.
"U.S. Appl. No. 15/867,789, Non Final Office Action mailed Apr. 2, 2020", 10 pgs.
"U.S. Appl. No. 15/867,801, Non Final Office Action mailed Sep. 30, 2019", 10 pgs.
"U.S. Appl. No. 15/867,801, Notice of Allowance mailed Feb. 5, 2020", 8 pgs.
"U.S. Appl. No. 15/867,801, Response filed Dec. 18, 2019 to Non Final Office Action mailed Sep. 30, 2019", 12 pgs.
"U.S. Appl. No. 15/867,873, Non Final Office Action mailed Apr. 3, 2020", 11 pgs.
"European Application Serial No. 18701908.8, Communication Pursuant to Article 94(3) EPC mailed May 20, 2020", 6 pgs.
"European Application Serial No. 18701908.8, Response to Communication Pursuant to Rules 161 and 162 filed Mar. 16, 2020", 8 pgs.
"European Application Serial No. 18702012.8, Response to Communication Pursuant to Rules 161 and 162 filed Mar. 11, 2020", 12 pgs.
"European Application Serial No. 18704105.8, Response to Communication Pursuant to Rules 161 and 162 filed Feb. 27, 2020", 10 pgs.
"International Application Serial No. PCT/US2017/048867, International Search Report mailed Nov. 13, 2017", 5 pgs.
"International Application Serial No. PCT/US2017/048867, Written Opinion mailed Nov. 13, 2017", 6 pgs.
"International Application Serial No. PCT/US2017/048896, International Search Report mailed Nov. 27, 2017", 5 pgs.
"International Application Serial No. PCT/US2017/048896, Written Opinion mailed Nov. 27, 2017", 6 pgs.
"International Application Serial No. PCT/US2017/052685, International Search Report mailed Jan. 4, 2018", 5 pgs.
"International Application Serial No. PCT/US2017/052685, Written Opinion mailed Jan. 4, 2018", 6 pgs.
"International Application Serial No. PCT/US2018/013251, International Preliminary Report on Patentability mailed Jul. 25, 2019", 7 pgs.
"International Application Serial No. PCT/US2018/013251, International Search Report mailed Apr. 12, 2018", 4 pgs.
"International Application Serial No. PCT/US2018/013251, Written Opinion mailed Apr. 12, 2018", 5 pgs.
"International Application Serial No. PCT/US2018/013257, International Preliminary Report on Patentability mailed Jul. 25, 2019", 8 pgs.
"International Application Serial No. PCT/US2018/013257, International Search Report mailed Apr. 19, 2018", 4 pgs.
"International Application Serial No. PCT/US2018/013257, Written Opinion mailed Apr. 19, 2018", 6 pgs.
"International Application Serial No. PCT/US2018/013268, International Preliminary Report on Patentability mailed Jul. 25, 2019", 13 pgs.
"International Application Serial No. PCT/US2018/013268, International Search Report mailed Apr. 30, 2018", 5 pgs.
"International Application Serial No. PCT/US2018/013268, Written Opinion mailed Apr. 30, 2018", 11 pgs.
Ahern, David K., et al., "Comparison of lumbar paravertebral EMG patterns in chronic low back pain patients and non-patient controls", Pain, 34, (1988), 153-160.
Allum, John H.J., et al., "A speedy solution for balance and gait analysis: angular velocity measured at the centre of body mass", Current Opinion in Neurology 18, (2005), 15-21.
Alo, Kenneth M., et al., "Effect of Spinal Cord Stimulation on Sensory Nerve Conduction Threshold Functional Measures", Neuromodulation, vol. 3, No. 3, (2000), 145-154.
Ambady, Nalini, et al., "Thin Slices of Expressive Behavior as Predictors of Interpersonal Consequences: a Meta-Analysis", Psychological Bulletin, 1992, vol. 111, No. 2, 256-274.

(56) References Cited

OTHER PUBLICATIONS

Annoni, Elizabeth M., et al., "Method and Apparatus for Pain Management Using Objective Pain Measure", U.S. Appl. No. 62/400,336, filed Sep. 27, 2016.
Annoni, Elizabeth M., et al., "Pain Management Based on Brain Activity Monitoring", U.S. Appl. No. 62/445,061, filed Jan. 11, 2017.
Annoni, Elizabeth M., et al., "Pain Management Based on Muscle Tension Measurements", U.S. Appl. No. 62/445,092, filed Jan. 11, 2017.
Annoni, Elizabeth M., et al., "Pain Management Based on Respiration-Mediated Heart Rates", U.S. Appl. No. 62/445,069, filed Jan. 11, 2017.
Annoni, Elizabeth M., et al., "Patient-Specific Calibration of Pain Quantification", U.S. Appl. No. 62/445,095, filed Jan. 11, 2017.
Arsenault, Marianne, et al., "Pain Modulation Induced by Respiration: Phase and Frequency Effects", Neuroscience 252, (2013), 501-511.
Artner, Juraj, et al., "Prevalence of sleep deprivation in patients with chronic neck and back pain: a retrospective evaluation of 1016 patients", Journal of Pain Research: 6, (2013), 1-6.
Ashraf, A B, et al., "The painful face—Pain expression recognition using active appearance models", Image and Vision Computing Elsevier Guildford, GB, vol. 27, No. 12, (Nov. 1, 2009), 1788-1796.
Bakker, Jorn, et al., "What's your current stress level? Detection of stress patterns from GSR sensor data", Eindhoven University of Technology—the Netherlands, (2011), 1-8.
Baliki, Marwan N., et al., "Beyond Feeling: Chronic Pain hurts the Brain, Disrupting the Default-Mode Network Dynamics", the Journal of Neuroscience, 28 (6), (Feb. 6, 2008), 1398-1403.
Banos, Oresti, et al., "PhysioDroid: Combining Wearable Health Sensors and Mobile Devices for a Ubiquitous, Continuous, and Personal Monitoring", the Scientific World Journal, vol. 2014 Article ID 190824, (2014), 11 pgs.
Bansevicius, Dalius, et al., "Mental stress of long duration: EMG activity, perceived tension, fatigue, and pain development in pain-free subjects", Headache: the Journal of Head and Face Pain; 37.8, (1997), 499-510.
Barad, Meredith J., et al., "Complex Regional Pain Syndrome Is Associated With Structural Abnormalities in Pain-Related Regions of the Human Brain", the Journal of Pain, vol. 15, No. 2, (Feb. 2014), 197-203.
Barkley, Jacob E., et al., "The effect of spinal cord stimulation unit revision on perceived pain, anxiety, mobility and physical activity in individuals with low back/lower extremity pain", Kent State University—the Spine and Pain Institute, Presented at Annual Meeting of the North American Neuromodulation Society (NANS) on Dec. 11-14, 2014, 1 pg.
Bartlett, Marian Stewart, et al., "Automatic Decoding of Facial Movements Reveals Deceptive Pain Expressions", Current Biology 24, 738-743, Mar. 31, 2014.
Beneck, George J., et al., "Spectral analysis of EMG using intramuscular electrodes reveals non-linear fatigability characteristics in persons with chronic low back pain", Journal of Electromyography and Kinesiology 23, (2013), 70-77.
Ben-Israel, Nir, et al., "Monitoring the nociception level: a multi-parameter approach", J Clin Monit Comput, (Jul. 2012), 10 pgs.
Ben-Israel, Nir, et al., "Monitoring the nociception level: a multi-parameter approach", J Clin Monit Comput 27, (2013), 659-668.
Boselli, E., et al., "Prediction of immediate postoperative pain using the analgesia/nociception index: a prospective observational study", British Journal of Anaesthesia 112 (4):, (2014), 715-721.
Boselli, E., et al., "Prospective observational study of the non-invasive assessment of immediate postoperative pain using the analgesia/nociception index (ANI)", British Journal of Anaesthesia 111, (2013), 453-459.
Broucqsault-Dédrie, Celine, et al., "Measurement of Heart Rate Variability to Assess Pain in Sedated Critically Ill Patients: a Prospective Observational Study", PLOS One, (Jan. 25, 2016), 1-11.
Chan, C. W.Y., et al., "Subjective pain sensation is linearly correlated with the Flexion reflex in man", Brain Research, 479, (1989), 145-150.
Chapman, C. Richard, et al., "Phasic pupil dilation response to noxious stimulation in normal volunteers: relationship to brain evoked potentials and pain report", (1999), 44-52.
Chen, Shuzhen, et al., "The role of the autonomic nervous system in hypertension: a bond graph model study", Physiological measurement 29.4 (2008): 473, (2008), 473-495.
Cheng, Qian, et al., "GaitTrack: Health Monitoring of Body Motion from Spatio-Temporal Parameters of Simple Smart Phones", the ACM Conference on Bioinformatics, Computational Biology, Biomed Biomedical Informatics (BCB) Health Information Symposium (HIS), Sep. 25, 2013,, (2013), 1-10.
Chuang, Chiung-Cheng, et al., "Photoplethysmography variability as an alternative approach to obtain heart rate variability information in chronic pain patient", J Clin Monit Comput—Published online, (Feb. 24, 2015), 1-6.
Chung, Ok Y., "Baroreflex sensitivity associated hypoalgesia in healthy states is altered by chronic pain", Pain 138, (2008), 87-97.
Ciampi De Andrade, Daniel, et al., "Neurophysiological assessment of spinal cord stimulation in failed back surgery syndrome", Pain 150, (2010), 485-491.
Cinaz, Burcu, et al., "Monitoring of mental workload levels during an everyday life office-work scenario", Pers Ubiquit Comput 17, (2013), 229-239.
Clark, Bryan Allen, et al., "Pain Management Based on Functional Measurements", U.S. Appl. No. 62/445,075, filed Jan. 11, 2017.
Culic, Ognjen, et al., "Serum activities of adenosine deaminase, dipeptidyl peptidase IV and prolyl endopeptidase in patients with fibromyalgia:diagnostic implications", Clin Rheumatol 35, (2016), 2565-2571.
Dansie, Elizabeth J., et al., "Activity in Adults with Chronic Widespread Pain", the Journal of Pain—Accepted Manuscript, (2014), 33 pgs.
Davydov, Dmitry M., et al., "Cardiovascular activity and chronic pain severity", Physiology & Behavior 152, 203-216 (2015).
De-La-Herran, Alvaro M., et al., "Gait Analysis Methods: an Overview of Wearable and Non-Wearable Systems, Highlighting Clinical Applications", Sensors 14, (2014), 3362-3394.
Denk, Franziska, et al., "Chronic Pain: Emerging Evidence for the Involvement of Epigenetics", Neuron 73 (3), (2012), 435-444.
Duschek, S., "Relationship between baroreceptor cardiac reflex sensitivity and pain experience in normotensive individuals", International Journal of Psychophysiology 65, (2007), 193-200.
Eisenberg, Elon, et al., "Quantitative Sensory Testing for Spinal Cord Stimulation in Patients With Chronic Neuropathic Pain", (2006), 161-165.
Elgendi, Mohamed, "On the analysis of fingertip photoplethysmogram signals", Current cardiology reviews 8.1, (2012), 14-25.
Evans, Subhadr, et al., "Heart rate variability as a biomarker for autonomic nervous system response differences between children with chronic pain and healthy control children", Journal of Pain Research 3.6, (2013), 449-457.
Fagius, J., et al., "The cold pressor test: effects on sympathetic nerve activity in human muscle and skin nerve fascicles", Acta physiologica Scandinavica 137.3, (1989), 325-334.
Fazalbhoy, Azharuddin, et al., "Individual differences in the cardiovascular responses to tonic muscle pain: parallel increases or decreases in muscle sympathetic nerve activity, blood pressure and heart rate", Exp Physiol 97.10, (2012), 1084-1092.
Frederiks, Joost, et al., "Within-subject electrocardiographic differences at equal heart rates: role of the autonomic nervous system", Pflügers Archiv 441.5, (2001), 717-724.
Geisser, Michael E., et al., "Pain-Related Fear, Lumbar Flexion, and Dynamic EMG Among Persons With Chronic Musculoskeletal Low Back Pain", Clin J Pain, vol. 20, No. 2, (Apr. 2004).
Generaal, Ellen, et al., "Reduced hypothalamic-pituitary-adrenal axis activity in chronic multi-site musculoskeletal pain: partly masked by depressive and anxiety disorders", BMC Musculoskeletal Disorders, 15:227, (2014), 1-11.

(56) References Cited

OTHER PUBLICATIONS

Gesche, Heiko, et al., "Continuous blood pressure measurement by using the pulse transit time: comparison to a cuff-based method", European journal of applied physiology 112.1, (2012), 309-315.

Godfrey, A., et al., "Direct measurement of human movement by accelerometry", Medical Engineering & Physics 30 (2008) 1364-1386.

Godfrey, A., et al., "Instrumenting gait with an accelerometer: a system and algorithm examination", Medical Engineering & Physics, Mar. 2015, doi:10.1016/j.medengphy.2015.02.003, 24 pgs.

Gouveia, S., et al., "Assessing Baroreflex Sensitivity in the Sequences Technique: Local versus Global Approach", Computers in Cardiology, 32, (2005), 279-282.

Granovsky, Yelena, et al., "Objective Correlate of Subjective Pain Perception by Contact Heat-Evoked Potentials", the Journal of Pain, vol. 9, No. 1, (Jan. 2008), 53-63.

Green, Alexande L., "Measurement of muscle sympathetic nerve activity reveals true sympathetic changes in chronic pain", Exp Physiol 97.10, (2012), 1083.

Hallman, David, et al., "Autonomic regulation, physical activity and perceived stress in subjects with musculoskeletal pain: 24-hour ambulatory monitoring", International Journal of Psychophysiology 86, (2012), 276-282.

Hallman, David M., et al., "Changes in physical activity and heart rate variability in chronic neck-shoulder pain: monitoring during work and leisure time", Int Arch Occup Environ Health 87, (2014), 735-744.

Hallman, David M., et al., "Long-Term Monitoring of Physical Behavior Reveals Different Cardiac Responses to Physical Activity among Subjects with and without Chronic Neck Pain", BioMed Research International, vol. 2015, Article ID 907482, 11 pages, http://dx.doi.org/10.1155/2015/907482, 11 pages.

Hartwich, Doreen, et al., "Effect of muscle metaboreflex activation on spontaneous cardiac baroreflex sensitivity during exercise in humans", J Physiol 589.24, (2011), 6157-6171.

Jensen, MP, et al., "Brain EEG activity correlates of chronic pain in persons with spinal cord injury: clinical implications", Nature; Spinal Cord; 51, (Jul. 17, 2012), 55-58.

Jess, Gunnar, et al., "Monitoring heart rate variability to assess experimentally induced pain using the analgesia nociception index—a randomised volunteer study", Eur J Anaesthesiol 32, (2015), 1-8.

Kang, Jon-Eun, et al., "Pulse transit time shows vascular changes caused by propofol in children", J Clin Monit Comput 29, (2015), 533-537.

Keefe, Francis J., et al., "An Objective Approach to Quantifing Pain Behavior and Gait Patterns in Low Back Pain Patients", Pain, 21, (1985), 153-161.

Kemler, Marius A., et al., "Impact of Spinal Cord Stimulation on Sensory Characteristics in Complex Regional Pain Syndrome Type 1—a Randomized Trial", Anesthesiology, 95, (2001), 72-80.

Keshari, Kayvan R., et al., "Lactic Acid and Proteoglycans as Metabolic Markers dor Discogenic Back Pain", Spine, vol. 13, No. 3, (2008), 312-317.

Kim, Young Uk, et al., "Pulse Transit Time as a Predictor of the Efficacy of a Celiac Plexus Block in Patients With Chronic Intractable Abdominal Pain", Clin J Pain, vol. 32, No. 6, (Jun. 2015), 522-526.

Kodituwakku, Sandun, et al., "Point Process Respiratory Sinus Arrhythmia Analysis during Deep Tissue Pain Stimulation", Computing in Cardiology 38, (2011), 193-196.

Koenig, J., et al., "Heart rate variability and experimentally induced pain in healthy adults: a systematic review", European Journal of Pain 18, (2014), 301-314.

Koenig, Julian, et al., "Chronic Pain and Heart Rate Variability in a Cross-Sectional Occupational Sample Evidence for Impaired Vagal Control", the Clinical Journal of Pain, Publish Ahead of Print, (2015), 31 pgs.

La Rovere, Maria Teresa, et al., "Baroreflex Sensitivity: Measurement and Clinical Implications", Ann Noninvasive Electrodardiol, 13(2):191-207, 2008.

Lamoth, Claudine J.C., et al., "How do persons with chronic low back pain speed up and slow down? Trunk-pelvis coordination and erector spinae activity during gait", Gait & Posture 23, (2006), 230-239.

Lamoth, Claudine J.C., et al., "Pelvis-Thorax Coordination in the Transverse Plane During Walking in Persons With Nonspecific Low Back Pain", Spine, vol. 27, No. 4, (2002), E92-E99.

Lane, James D., et al., "Respiratory Sinus Arrhythmia and Cardiovascular Responses to Stress", Psychophysiology, vol. 29, No. 4, (1992), 461-470.

Latremoliere, Alban, et al., "Reduction of Neuropathic and Inflammatory Pain through Inhibition of the Tetrahydrobiopterin Pathway", Neuron, 86 (6), (2015), 1393-1406.

Ledowski, Thomas, et al., "The influence of age and sex on the relationship between heart rate variability, haemodynamic variables and subjective measures of acute post-operative pain", European Journal of Anaesthesiology, vol. 28, No. 6, (2011), 433-437.

Lee, Jihyoung, et al., "Validation of normalized pulse volume in the outer ear as a simple measure of sympathetic activity using warm and cold pressor tests: towards applications in ambulatory monitoring", Physiol. Meas. 34, (2013), 359-375.

Lidberg, Lars, et al., "Sympathetic Skin Nerve Dischai gcs in Relation lo Aniplliule ol Skin Resistance Responses", Psychophysiology, vol. 18, No. 3, (May 1981), 268-270.

Littlewort, Gwen C., et al., "Automatic Coding of Facial Expressions Displayed During Posed and Genuine Pain", Image and Vision Computing, 27(12) p. 1741-1844.

Logier, R., et al., "PhysioDoloris: a monitoring device for Analgesia / Nociception balance evaluation using Heart Rate Variability analysis", 32nd Annual International Conference of the IEEE EMBS, (2010), 1194-1197.

Looney, David, et al., "The In-the-Ear Recording Concept", IEEE Pulse Nov./Dec. 2012, 32-42.

Marchi, Antonio, et al., "Pain Biomarkers", Clin Drug Invest, 29 Suppl 1, (2009), 41-46.

Martini, Chris H., et al., "Ability of the Nociception Level, a Multiparameter Composite of Autonomic Signals, to Detect Noxious Stimuli during Propofol-Remifentanil Anesthesia", Anesthesiology, vol. 123, No. 3, (2015), 524-534.

Mauer, C., et al., "Quantitative sensory testing in the German Research Network on Neuropathic Pain (DFNS): Somatosensory abnormalities in 1236 patients with different neuropathic pain syndromes", Pain 150, (2010), 439-450.

McBeth, John, et al., "Hypothalamic-pituitary-adrenal stress axis function and the relationship with chronic widespread pain and its antecedents", [Online]. Retrieved from the Internet: <URL: http://arthritis-research.com/content/7/5/R992, (2005), R992-R1000.

McCarthy, K. F., et al., "Cerebrospinal fluid levels of glial cell-derived neurotrophic factor correlate with spinal cord stimulation frequency in patients with neuropathic pain: a preliminary report", Spinal Cord 52, (2014), S8-S10.

McCracken, Lance M., et al., "Disrupted sleep patterns and daily functioning in patients with chronic pain", Pain Res Manage vol. 7 No. 2 Summer 2002 75-79.

Mikkelsen, Kaare B., et al., "EEGRecordedfromtheEar:CharacterizingtheEar-EEGMethod", FrontiersinNeuroscience|www.frontiersin.org, Nov. 2015|vol. 9|Article438, 8 pgs.

Mironer, Y. Eugene, et al., "Pain Tolerance Threshold: a Pilot Study of an Objective Measurement of Spinal Cord Stimulator Trial Results", Pain Medicine, vol. 1, No. 2, (2000), 110-115.

Moseley, G. Lorimer, et al., "Tactile Discrimination, but not tactile stimulation alone, reduces chronic limg pain", Pain 137, (2008), 600-608.

Moxham, I.M., "Understanding Arterial Pressure Waveforms", Southern African Journal of Anaesthesia and Analgesia 9.1, (2003), 40-42.

Mukkamala, R., et al., "Toward ubiquitous blood pressure monitoring via pulse transit time: theory and practice", IEEE Transactions on Biomedical Engineering 62.8, (2015), 1879-1901.

Mylius, Vett, et al., "Sex differences in nociceptive withdrawal reflex and pain perception", Somatosensory and Motor Research 22 (3), (Sep. 2005), 207-211.

(56) References Cited

OTHER PUBLICATIONS

Neblett, Randy, et al., "What Is the Best Surface EMG Measure of Lumbar Flexion-Relation for Distinguishing Chronic Low Back Pain Patients From Pain-Free Controls?", Clin J Pain 29 (4)—NIH Public Access, (Apr. 2013), 334-340.

Ng, Joseph, et al., "EMG activity of trunk muscles and torque output during isometric axial rotation exertion: a comparison between back pain patients and matched controls", Journal of Orthopaedic Research; 20, (2002), 112-121.

Palermo, Tonya M., et al., "Subjective Sleep Disturbances in Adolescents With Chronic Pain: Relationship to Daily Functioning and Quality of Life", the Journal of Pain, vol. 6, No. 3, (March 2995), 201-207.

Panjabi, Manohar, "Clinical spinal instability and low back pain", Journal of Electromyography and Kinesiology 13, (2003), 371-379.

Patti, Gary J., et al., "Metabolomics implicates altered sphingolipids in chronic pain of neuropathic origin", nature chemical biology, vol. 8, (Mar. 2012), 232-234.

Perruchoud, Christophe, et al., "Assessment of Physical Activity of Patients with Chronic Pain", Neuromodulation: Technology at the Neural Interface; 17, (2012), 42-47.

Pinheiro, Eulália Silva Dos Santos, et al., "Electroencephalographic Patterns in Chronic Pain: a Systematic Review of the Literature", Plos One |DOI:10.1371/journal.pone.0149085 Feb. 25, 2016, 27 pgs.

Plaza-Manzano, Gustavo, et al., "Changes in Biochemical Markers of Pain Perception and Stress Response After Spinal Manipulation", Journal of Orthopaedic & Sports Physical Therapy, vol. 44, No. 4, (Apr. 2014), 231-239.

Pleger, Burkhard, et al., "Patterns of cortical reorginization parallel impaired tactile discrimination and pain intensity in complex regional pain syndrome", NeuroImage 32, (2006), 503-510.

Pluijms, Wouter A., et al., "Increased Contact Heat Evoked Potential Stimulation Latencies in Responders to Spinal Cord Stimulation for Painful Diabetic Cord Stimulation for Painful Diabetic Cord Stimulation for Painful Diabetic Polyneuropathy", Neuromodulation 18, (2015), 126-132.

Poon, C.C.Y., "Cuff-less and noninvasive measurements of arterial blood pressure by pulse transit time", 2005 IEEE Engineering in Medicine and Biology 27th Annual Conference. IEEE, 2006., (2006), 5877-5880.

Prichep, Leslie S., et al., "Evaluation of the Pain Matrix Using EEG Source Localization: a Feasibility Study", Pain Medicine 12, (2011), 1241-1248.

Prkachin, Kenneth, "The consistency of facial expressions of pain: a comparison across modalities", PAIN, 51, (1992), 279-306.

Raminen, Tina, et al., "The Impact of Spinal Cord Stimulation on Sleep Patterns", Neuromodulation 19, (2016), 477-481.

Rasche, Dirk, et al., "Quantitative Sensory Testing in Patients With Chronic Unilateral Radicular Neuropathic Pain and Active Spinal Cord Stimulation", Neuromodulation, vol. 9, No. 3, (2006), 239-247.

Rhudy, Jamie L., et al., "Defining the nociceptive flexion reflex (NFR) threshold in human participants: a comparison of different scoring criteria", Pain 128, (2007), 244-253.

Roy, Sourav Dey, et al., "An Approach for Automatic Pain Detection through Facial Expression", Procedia Computer Science 84 (2016) 99-106.

Sacco, Marcella, et al., "The Relationship Between Blood Pressure and Pain", the Journal of Clinical Hypertension vol. 15, No. 8, (Aug. 2013), 600-605.

Sarnthein, Johannes, et al., "Increased EEG power and slowed dominant frequncy in patients with neurogenic pain", Brain 129, (2005), 55-64.

Sato, Karina L/, et al., "Spinal Cord Stimulation (SCS) Improves Decreased Physical Activity Induced by Nerve Injury", Behavioral Neuroscience, vol. 128, No. 5, (2914), 625-632.

Sawada, Yukihiro, et al., "Normalized pulse volume (NPV) derived photo-plethysmography as a more valid measure of the finger vascular tone", International Journal of Psychophysiology 41, (2001), 1-10.

Sayar, Kemal, et al., "Sleep Quality in Chronic Pain Patients", Can J. Psychiatry, vol. 47, No. 9, (Nov. 2002), 844-848.

Schulman, Joshua J., et al., "Thalamocortical dysrhythmia syndrome: MEG imaging of neuropathic pain", (Jul. 25, 2014), 33-39.

Schulz, Enrico, et al., "Prefrontal Gamma Oscillations Encode Tonic Pain in Humans", Cerebral Cortex 2015, (Mar. 8, 2015), 1-8.

Sesay, Musa, et al., "Responses of Heart Rate Variability to Acute Pain After Minor Spinal Surgery: Optimal Thresholds and Correlation With the Numeric Rating Scale", J Neurosurg Anesthesiol, vol. 00, No. 00, (2014), 1-7.

Shouldice, R., "PR and PP ECG intervals as indicators of autonomic nervous innervation of the cardiac sinoatrial and atrioventricular nodes", Neural Engineering, 2003. Conference Proceedings. First International IEEE EMBS Conference on. IEEE, (Mar. 2003), 261-264.

Siddall, Phillip J., et al., "Magnetic Resonance Spectroscopy Detects Biochemical Changes in the Brain Associated with Chronic Low Back Pain: a Preliminary Report", Anesth Analg 102, (2006), 1164-1168.

Sihvonen, T., et al., "Electric behavior of low back muscles during lumbar pelvic rhythm in low back pain patients and healthy controls", Archives of physical medicine and rehabilitation; 72.13, (1991), 1080-1087.

Simoes, Mario A., "Feasibility of Wearable Sensors to Determine Gait Parameters", University of South Florida Scholar Commons, (2011), 1-98.

Skljarevski, V., et al., "The nociceptive flexion reflex in humans—review article", Pain, 96, (2002), 3-8.

Smallwood, Rachel F., et al., "Structural Brain Anomalies and Chronic Pain: a Quantitative Meta-Analysis of Gray Matter Volume", the Journal of Pain, vol. 14, No. 7, (Jul. 2013), 663-675.

Sotocinal, S G, et al., "The Rat Grimace Scale partially automated method for quantifying pain in the laboratory rat via facial expressions", Molecular Pain Biomed Central, London, GB, vol. 7 no. 1, (Jul. 29, 2011), 1744-8069.

Srivastava, Kyle Harish, et al., "Pain Management Based on Cardiovascular Parameters", U.S. Appl. No. 62/445,053, filed Jan. 11, 2017.

Srivastava, Kyle Harish, et al., "Pain Management Based on Emotional Expression Measurements", U.S. Appl. No. 62/445,082, filed Jan. 11, 2017.

Staud, Roland, "Heart rate variability as a biomarker of fibromyalgia syndrome", Fut Rheumatol 3 (5)—NIH Public Access, (Oct. 1, 2008), 475-483.

Storm, H., et al., "Skin conductance correlates with perioperative stress", Acta Anaesthesiol Scand 46, (2002), 887-895.

Sturgeon, John A., et al., "Respiratory Sinus Arrhythmia: a Marker of Resilience to Pain Induction", Int.J. Behav. Med. 21, (2014), 961-965.

Swenne, C. A., "Baroreflex sensitivity: mechanisms and measurement", Neth Heart J 21, (2013), 58-60.

Symons, Frank J., et al., "Can Biomarkers Differentiate Pain and No Pain Subgroups of Nonverbal Children with Cerebral Palsy? a Preliminary Investigation Based on Noninvasive Saliva Sampling", Pain Med 16 (2), (2015), 249-256.

Tagliazucchi, Enzo, et al., "Brain resting state is disrupted in chronic back pain patients", Neurosci Lett. 485 (1)—NIH Public Access, (Nov. 12, 2010), 26-31.

Tao, Weijun, et al., "Gait Analysis Using Wearable Sensors", Sensors 12, (2012), 2255-2283.

Tauda, Makoto, et al., "P2X4receptorsandneuropathicpain", Frontiers in Cellular Neuroscience, vol. 7, Article 191, (Oct. 28, 2013), 1-6.

Terkelsen, Astrid J., et al., "Heart Rate Variability in Complex Regional Pain Syndrome during Rest and Mental and Orthostatic Stress", Anesthesiology, vol. 116, No. 1, (Jan. 2012), 133-146.

Thakur, Pramodsingh Hirasingh, et al., "Method and Apparatus for Pain Control Using Baroreflex Sensitivity During Posture Change", U.S. Appl. No. 62/412,587, filed Oct. 25, 2016.

(56) References Cited

OTHER PUBLICATIONS

Thakur, Pramodsingh Hirasingh, et al., "Systems and Methods for Closed-Loop Pain Management", U.S. Appl. No. 62/400,313, filed Sep. 27, 2016.
Thankur, Pramodsingh Hirasingh, et al., "Method and Apparatus for Pain Management Using Heart Sounds", U.S. Appl. No. 62/395,641, filed Sep. 16, 2016.
Theuvenel, Peter J., et al., "Responses to Median and Tbial Nerve Stimulation in Patients with Chronic Neuropathic Pain", Brain Topography, vol. 11, No. 4, (1999), 306-313.
Uceyler, Nuncan, et al., "Differential expression of cytokines in painful and painless neuropathies", (2007).
Uzar, E., et al., "Serum cytokine and pro-brain natriuretic peptide (BNP) levels in patients with migraine", European Review for Medical and Pharmacological Sciences; 15, (2011), 1111-1116.
Van Velzen, Marit H.N., et al., "Effect of heat-induced pain stimuli on pulse transit time and pulse wave amplitude in healthy volunteers", Physiological Measurement 37, (2016), 52-66.
Villarejo, Viqueira Maria, et al., "A Stress Sensor Based on Galvanic Skin Response (GSR) Controlled by ZigBee", Sensors 12, (2012), 6075-6101.
Walton, K. D., et al., "Abnormal thalamocortical activity in patients with Complex Regional Pain Syndrome (CRPS) Type 1", Pain 150, (2010), 41-51.
Willer, Jean Claude, "Comparative Study of Perceived Pain and Nociceptive Flexion Reflex in Man", Pain, 3, (1977), 69-80.
Williams, Dewayne P., et al., "Effects of Chronic Pelvic Pain on Heart Rate Variability in Women", the Journal of Urology, vol. 194,, (Nov. 2015), 1-6.
Wong, Arnold Y.L., et al., "Does experimental low back pain change posteroanterior lumbar spinal stiffness and trunk muscle activity? a randomized crossover study", Clinical Biomechanics 34, (2016), 45-52.
Wong, Jih-Sen, et al., "A comparative study of pulse rate variability and heart rate variability in healthy subjects", J Clin Monit Comput 26, (2012), 107-114.
Wu, Hao-Yu, et al., "Eulerian Video Magnification for Revealing Subtle Changes in the World", ACM Transactions on Graphics 31(4), (2012), 1-8.
Zamuner, Antonio R., et al., "Respiratory Sinus Arrhythmia and its Association with Pain in Women with Fibromyalgia Syndrome", Pain Practice, vol. 16, Issue 6, (2016), 704-711.
Zamunér, A. R., et al., "Relationship between sympathetic activity and pain intensity in fibromyalgia", Clin Exp Rheumatol 33—Abstract, [Online]. Retrieved from the Internet: <URL: http://www.ncbi.nlm.nih.gov.ezp3.lib.umn.edu/pubmed/25786044, (Feb. 2015), 1-2.
Zeng, Zhihong, et al., "A Survey of Affect Recognition Methods: Audio, Visual and Spontaneous Expressions", ICMI'07, Nov. 12-15, 2007, 126-133.
Zhang, John, "Effect of Chiropractic Care on Heart Rate Variability and Pain in a Multisite Clinical Study", Jimmal of Manipulative and Physiological Therapeutics, vol. 29, No. 4, (2006), 267-274.
Zhou, Jing, et al., "Recurrent Convolutional Neural Network Regression for Continuous Pain Intensity Estimation in Video", arXiv preprint arXiv: 1605.00894 (2016) 84-92.
Zhou, Jing, et al., "Recurrent Convolutional Neural Network Regression for Continuous Pain Intensity Estimation in Video", Technical Report, (May 3, 2016), 1-11.
U.S. Appl. No. 18/077,981 U.S. Pat. No. 11,857,794, filed Dec. 8, 2022, Pain Management Based on Brain Activity Monitoring.
U.S. Appl. No. 18/085,270, filed Dec. 20, 2022, Pain Management Based on Emotional Expression Measurements.
"International Application Serial No. PCT US2017 057367, International Search Report mailed Jan. 19, 2018", 4 pgs.
"International Application Serial No. PCT US2017 057367, Written Opinion mailed Jan. 19, 2018", 4 pgs.
"International Application Serial No. PCT US2018 041860, International Search Report mailed Oct. 17, 2018", 4 pgs.
"International Application Serial No. PCT US2018 041860, Written Opinion mailed Oct. 17, 2018", 5 pgs.
"International Application Serial No. PCT US2017 048867, International Preliminary Report on Patentability mailed Mar. 28, 2019", 8 pgs.
"International Application Serial No. PCT US2017 052685, International Preliminary Report on Patentability mailed Apr. 11, 2019", 6 pgs.
"International Application Serial No. PCT US2017 048896, International Preliminary Report on Patentability mailed Apr. 11, 2019", 8 pgs.
"International Application Serial No. PCT US2017 057367, International Preliminary Report on Patentability mailed May 9, 2019", 6 pgs.
"Australian Application Serial No. 2017325823, First Examination Report mailed Jun. 19, 2019", 3 pgs.
"Australian Application Serial No. 2017334841, First Examination Report mailed Jun. 24, 2019", 3 pgs.
"Australian Application Serial No. 2017335497, First Examination Report mailed Jun. 26, 2019", 3 pgs.
"European Application Serial No. 17762308.9, Response to Communication pursuant to Rules 161 and 162 filed Nov. 26, 2019", 23 pgs.
"Australian Application Serial No. 2017335497, Response filed Nov. 27, 2019 to First Examination Report mailed Jun. 26, 2019", 18 pgs.
"European Application Serial No. 17794503.7, Response to Communication Pursuant to Rules 161 and 162 filed Dec. 30, 2019", 11 pgs.
"International Application Serial No. PCT US2018 041860, International Preliminary Report on Patentability mailed Jan. 30, 2020", 7 pgs.
"Australian Application Serial No. 2017334841, Response filed Feb. 6, 2020 to First Examination Report mailed Jun. 24, 2019", 14 pgs.
"European Application Serial No. 17778108.5, Response to Communication Pursuant to Rules 161 and 162 filed Dec. 2, 2019", 3 pgs.
"European Application Serial No. 18701908.8, Response filed Sep. 29, 2020 to Communication Pursuant to Article 94(3) EPC mailed May 20, 2020", 29 pgs.
"European Application Serial No. 18704105.8, Communication Pursuant to Article 94(3) EPC mailed Jan. 5, 2022", 9 pgs.
"U.S. Appl. No. 16/848,580, Response filed Feb. 2, 2022 to Non Final Office Action mailed Jan. 4, 2022", 11 pgs.
"European Application Serial No. 18704105.8, Response filed May 6, 2022 to Communication Pursuant to Article 94(3) EPC mailed Jan. 5, 2022", 35 pgs.
"U.S. Appl. No. 16/848,580, Response filed Jun. 27, 2022 to Final Office Action mailed May 10, 2022", 12 pgs.
"U.S. Appl. No. 17/145,514, Non Final Office Action mailed Aug. 4, 2022", 7 pgs.
"U.S. Appl. No. 16/848,580, Notice of Allowance mailed Aug. 31, 2022", 8 pgs.
"U.S. Appl. No. 17/145,514, Examiner Interview Summary mailed Sep. 14, 2022", 2 pgs.
"U.S. Appl. No. 17/145,514, Response filed Sep. 26, 2022 to Non Final Office Action mailed Aug. 4, 2022", 8 pgs.
"U.S. Appl. No. 17/145,514, Notice of Allowance mailed Oct. 5, 2022", 5 pgs.
"U.S. Appl. No. 17/145,514, Examiner Interview Summary mailed Jan. 18, 2023", 2 pgs.
"European Application Serial No. 18702012.8, Communication Pursuant to Article 94(3) EPC mailed Jan. 25, 2023", 5 pgs.
"U.S. Appl. No. 18/077,981, Non Final Office Action mailed May 25, 2023", 7 pgs.
"U.S. Appl. No. 18/077,981, Response filed Jun. 8, 2023 to Non Final Office Action mailed May 25, 2023", 7 pgs.
"U.S. Appl. No. 18/077,981, Notice of Allowance mailed Jul. 7, 2023", 7 pgs.
Berthomier, Christian, "Automatic analysis of single-channel sleep EEG: validation in healthy individuals", Sleep—New York Then Westchester—30.11, (2007), 1587-1595.

(56) References Cited

OTHER PUBLICATIONS

Bunde, Armin, "Correlated and uncorrelated regions in heart-rate fluctuations during sleep", Physical Review Letters 85.17, (2000), 3736-3739.
Foo, H., "Brainstem modulation of pain during sleep and waking", Sleep medicine reviews 7.2, (2003), 145-154.
Sano, Akane, "Quantitative analysis of wrist electrodermal activity during sleep", Int J Psychophysiol Dec. 2014 94 3, (2014), 8 pages.
"U.S. Appl. No. 15/687,925, Non Final Office Action mailed Oct. 9, 2018", 9 pgs.
"U.S. Appl. No. 15/687,925, Response filed Jan. 9, 2019 to Non Final Office Action mailed Oct. 9, 2018", 9 pgs.
"U.S. Appl. No. 15/688,676, Non Final Office Action mailed Jan. 11, 2019", 7 pgs.
"U.S. Appl. No. 15/687,925, Final Office Action mailed Feb. 14, 2019", 10 pgs.
"U.S. Appl. No. 15/688,676, Response filed Apr. 9, 2019 to Non Final Office Action mailed Jan. 11, 2019", 12 pgs.
"U.S. Appl. No. 15/687,925, Response filed May 13, 2019 to Final Office Action mailed Feb. 14, 2019", 11 pgs.
"U.S. Appl. No. 15/711,578, Non Final Office Action mailed May 23, 2019", 6 pgs.
"U.S. Appl. No. 15/687,925, Non Final Office Action mailed Jun. 11, 2019", 11 pgs.
"U.S. Appl. No. 15/788,403, Non Final Office Action mailed Jul. 23, 2019", 9 pgs.
"U.S. Appl. No. 15/688,676, Final Office Action mailed Jul. 29, 2019", 7 pgs.
"U.S. Appl. No. 15/711,578, Repsonse filed Aug. 23, 2019 to Non Final Office Action mailed May 23, 2019", 11 pgs.
"U.S. Appl. No. 15/711,578, Examiner Interview Summary mailed Aug. 28, 2019", 3 pgs.
"U.S. Appl. No. 15/711,578, Supplemental Response filed Aug. 28, 2019 to Non Final Office Action mailed May 23, 2019", 11 pgs.
"U.S. Appl. No. 15/888,808, Non Final Office Action mailed Sep. 11, 2019", 7 pgs.
"U.S. Appl. No. 15/688,676, Examiner Interview Summary mailed Sep. 25, 2019", 3 pgs.
"U.S. Appl. No. 15/688,676, Response filed Sep. 25, 2019 to Final Office Action mailed Jul. 29, 2019", 10 pgs.
"U.S. Appl. No. 15/788,403, Response filed Oct. 8, 2019 to Non Final Office Action mailed Jul. 23, 2019", 11 pgs.
"U.S. Appl. No. 15/688,676, Non Final Office Action mailed Oct. 30, 2019", 6 pgs.
"U.S. Appl. No. 15/888,808, Response filed Nov. 19, 2019 to Non Final Office Action mailed Sep. 11, 2019", 10 pgs.
"U.S. Appl. No. 15/888,808, Examiner Interview Summary mailed Nov. 21, 2019", 3 pgs.
"U.S. Appl. No. 15/711,578, Notice of Allowance mailed Nov. 25, 2019", 7 pgs.
"U.S. Appl. No. 15/888,808, Final Office Action mailed Dec. 16, 2019", 7 pgs.
"U.S. Appl. No. 15/688,676, Response filed Jan. 7, 2020 to Non Final Office Action mailed Oct. 30, 2019", 10 pgs.
"U.S. Appl. No. 15/788,403, Notice of Allowance mailed Jan. 23, 2020", 7 pgs.
"U.S. Appl. No. 15/888,808, Response filed Jan. 31, 2020 to Final Office Action mailed Dec. 16, 2019", 11 pgs.
"U.S. Appl. No. 15/888,808, Advisory Action mailed Feb. 10, 2020", 2 pgs.
"U.S. Appl. No. 15/888,808, Response filed Mar. 16, 2020 to Advisory Action mailed Feb. 10, 2020", 8 pgs.
"U.S. Appl. No. 15/788,403, Corrected Notice of Allowability mailed Mar. 18, 2020", 2 pgs.
"U.S. Appl. No. 16/034,304, Non Final Office Action mailed Apr. 3, 2020", 15 pgs.
"U.S. Appl. No. 15/688,676, Notice of Allowance mailed Apr. 14, 2020", 7 pgs.
"U.S. Appl. No. 15/788,403, 312 Amendment filed Apr. 22, 2020", 8 pgs.
"U.S. Appl. No. 15/788,403, PTO Response to Rule 312 Communication mailed Apr. 30, 2020", 2 pgs.
"U.S. Appl. No. 15/867,873, Response filed Jun. 30, 2020 to Non Final Office Action mailed Apr. 1, 2020", 10 pgs.
"U.S. Appl. No. 16/034,304, Response filed Jun. 30, 2020 to Non Final Office Action mailed Apr. 3, 2020", 13 pgs.
"U.S. Appl. No. 15/888,808, Non Final Office Action mailed Jul. 2, 2020", 11 pgs.
"U.S. Appl. No. 16/034,304, Final Office Action mailed Jul. 27, 2020", 11 pgs.
"U.S. Appl. No. 15/888,808, Examiner Interview Summary mailed Aug. 3, 2020", 3 pgs.
"U.S. Appl. No. 16/034,304, Examiner Interview Summary mailed Sep. 15, 2020", 3 pgs.
"U.S. Appl. No. 16/034,304, Response filed Sep. 16, 2020 to Final Office Action mailed Jul. 27, 2020", 11 pgs.
"U.S. Appl. No. 16/034,304, Notice of Allowance mailed Sep. 29, 2020", 8 pgs.
"U.S. Appl. No. 15/888,808, Response filed Sep. 29, 2020 to Non Final Office Action mailed Jul. 2, 2020", 11 pgs.
"U.S. Appl. No. 15/867,873, Notice of Allowance mailed Oct. 22, 2020", 5 pgs.
"U.S. Appl. No. 15/888,808, Notice of Allowance mailed Nov. 30, 2020", 9 pgs.
"U.S. Appl. No. 16/821, 161, Non Final Office Action mailed Jan. 3, 2022", 5 pgs.
"U.S. Appl. No. 16/848,580, Non Final Office Action mailed Jan. 4, 2022", 14 pgs.
"U.S. Appl. No. 16/821, 161, Response filed Jan. 27, 2022 to Non Final Office Action mailed Jan. 3, 2022", 8 pgs.
"U.S. Appl. No. 16/848,580, Examiner Interview Summary mailed Feb. 4, 2022", 3 pgs.
"U.S. Appl. No. 16/821, 161, Notice of Allowance mailed Apr. 4, 2022", 7 pgs.
"U.S. Appl. No. 16/848,580, Final Office Action mailed May 10, 2022", 17 pgs.
"U.S. Appl. No. 16/848,580, Examiner Interview Summary mailed Jun. 29, 2022", 2 pgs.
"U.S. Appl. No. 18/085,270, Non Final Office Action mailed Jun. 17, 2024", 8 pgs.

\* cited by examiner

PATIENT-SPECIFIC CALIBRATION OF PAIN QUANTIFICATION

CLAIM OF PRIORITY

This application is a continuation of U.S. application Ser. No. 15/867,772, filed Jan. 11, 2018, which claims the benefit of priority under 35 U.S.C. § 119(e) of U.S. Provisional Patent Application Ser. No. 62/445,095, filed on Jan. 11, 2017, which are herein incorporated by reference in their entireties.

CROSS REFERENCE TO RELATED APPLICATIONS

This application is related to commonly assigned U.S. Provisional Patent Application Ser. No. 62/445,053, entitled "PAIN MANAGEMENT USING CARDIOVASCULAR PARAMETERS", filed on Jan. 11, 2017, U.S. Provisional Patent Application Ser. No. 62/445,061, entitled "PAIN MANAGEMENT BASED ON BRAIN ACTIVITY MONITORING", filed on Jan. 11, 2017, U.S. Provisional Patent Application Ser. No. 62/445,069, entitled "PAIN MANAGEMENT BASED ON RESPIRATION-MEDIATED HEART RATES", filed on Jan. 11, 2017, U.S. Provisional Patent Application Ser. No. 62/445,075, entitled "PAIN MANAGEMENT BASED ON FUNCTIONAL MEASUREMENTS", filed on Jan. 11, 2017, U.S. Provisional Patent Application Ser. No. 62/445,082, entitled "PAIN MANAGEMENT BASED ON EMOTIONAL EXPRESSION MEASUREMENTS", filed on Jan. 11, 2017, U.S. Provisional Patent Application Ser. No. 62/445,092, entitled "PAIN MANAGEMENT BASED ON MUSCLE PENSION MEASUREMENTS", filed on Jan. 11, 2017, U.S. Provisional Patent Application Ser. No. 62/395,641, entitled "METHOD AND APPARATUS FOR PAIN MANAGEMENT USING HEART SOUNDS", filed on Sep. 16, 2016, U.S. Provisional Patent Application Ser. No. 62/400,313, entitled "SYSTEMS AND METHODS FOR CLOSED-LOOP PAIN MANAGEMENT", filed on Sep. 27, 2016, U.S. Provisional Patent Application Ser. No. 62/400,336, entitled "METHOD AND APPARATUS FOR PAIN MANAGEMENT USING OBJECTIVE PAIN MEASURE", filed on Sep. 27, 2016, U.S. Provisional Patent Application Ser. No. 62/412,587, entitled "METHOD AND APPARATUS FOR PAIN CONTROL USING BAROREFLEX SENSITIVITY DURING POSTURE CHANGE", filed on Oct. 25, 2016, which are incorporated by reference in their entireties.

TECHNICAL FIELD

This document relates generally to medical systems and more particularly to systems, devices, and methods for pain management.

BACKGROUND

Pain is one of the most common and among the most personally compelling reasons for seeking medical attention, and consumes considerable healthcare resources each year. The relation between etiology, underlying mechanisms and the specific symptoms and signs related to painful disorders is complex. Pain in an individual patient may be produced by more than one mechanism.

Chronic pain, such as pain present most of the time for a period of six months or longer during the prior year, is a highly pervasive complaint and consistently associated with psychological illness. Chronic pain may originate with a trauma, injury or infection, or there may be an ongoing cause of pain. Chronic pain may also present in the absence of any past injury or evidence of body damage. Common chronic pain can include headache, low back pain, cancer pain, arthritis pain, neurogenic pain (pain resulting from damage to the peripheral nerves or to the central nervous system), or psychogenic pain (pain not due to past disease or injury or any visible sign of damage inside or outside the nervous system).

Chronic pain may be treated or alleviated using medications, acupuncture, surgery, and neuromodulation therapy such as local electrical stimulation or brain stimulation, among others. Examples of neuromodulation include Spinal Cord Stimulation (SCS), Deep Brain Stimulation (DBS), Peripheral Nerve Stimulation (PNS), and Functional Electrical Stimulation (FES). Implantable neuromodulation systems have been applied to deliver such a therapy. An implantable neuromodulation system may include an implantable neurostimulator, also referred to as an implantable pulse generator (IPG), which can electrically stimulate tissue or nerve centers to treat nervous or muscular disorders. In an example, an IPG can deliver electrical pulses to a specific region in a patient spinal cord, such as particular spinal nerve roots or nerve bundles, to create an analgesic effect that masks pain sensation.

SUMMARY

By way of example, chronic pain management may involve determining appropriate treatment regimens such as SCS and evaluating therapy efficacy. Accurate pain assessment and characterization are desirable for managing patients with chronic pain. Pain may be assessed from patient physiological or functional responses, such as sensed using one or more sensors. A composite pain score, which characterizes patient overall pain perception, may be generated using a combination of sensor-based pain indicators. However, patient health status may change over time. For example, a patient may increase or decrease their daily exercise level, develop comorbidities, or experience worsening or improvement of their existing chronic diseases, among other health status changes. The changes in patient health condition or daily routines may alter the patient physiological or functional responses to pain. For example, a physiological signal that used to be sensitive to, and thus more indicative of, pain intensity may become less sensitive thus less indicative of pain intensity when there are gradual changes in patient health condition or daily routines. The present inventors have recognized that there remains a demand for improving pain management, such as an objective, sensor-based pain assessment that can adapt to changes in patient physiological or functional response to pain. Additionally, in an automated closed-loop pain therapy system that uses pain therapy efficacy as a feedback for therapy control, the therapy efficacy may be evaluated based on sensor-based pain assessment. It is desirable that sensors and the pain assessment mechanism be calibrated to account for changes in patient health status or changes in patient daily routines, so as to allow for timely and individualized pain therapy titration.

This document discusses, among other things, systems, devices, and methods for assessing pain in a subject. The system may include sensors to sense from the patient a plurality of physiological or functional signals corresponding to multiple pain intensities. A pain analyzer may generate a pain score using the sensed physiological or functional signals and a fusion model. The fusion model may algorithmically combine the sensed physiological or functional signals. The system may calibrate the fusion model based on measurements from the plurality of physiological or functional signals and a reference pain quantification that corresponds to the multiple pain intensities. The reference pain quantification may be produced through a pain induction process, or derived from patient spontaneous pain episodes. The pain analyzer may generate a pain score using the calibrated fusion model. The system may include a neurostimulator that adaptively controls delivery of pain therapy based on the pain score.

Example 1 is a system for managing pain of a patient. The system comprise: a sensor circuit coupled to one or more sensors configured to sense from the patient a plurality of physiological or functional signals corresponding to multiple pain intensities; a pain analyzer circuit coupled to the sensor circuit and configured to generate a pain score using the sensed plurality of the physiological or functional signals and a fusion model; a calibration circuit configured to establish or update the fusion model based on (1) measurements from the plurality of physiological or functional signals corresponding to the multiple pain intensities and (2) a reference pain quantification corresponding to the multiple pain intensities; a controller circuit configured to control the pain analyzer circuit to generate a pain score using the established or updated fusion model; and an output unit configured to output the pain score to a user or a process.

In Example 2, the subject matter of Example 1 optionally includes an electrostimulator that may be configured to generate electrostimulation energy to treat pain. The controller circuit may be configured to control the electrostimulator to deliver a pain therapy and to control the electrostimulation energy generated by the electrostimulator according to the pain score.

In Example 3, the subject matter of Example 2 optionally includes the electrostimulator that may be further configured to deliver at least one of: a spinal cord stimulation; a brain stimulation; or a peripheral nerve stimulation.

In Example 4, the subject matter of any one or more of Examples 2-3 optionally includes the controller circuit that may be further configured to deliver first electrostimulation to the patient in response to the pain score exceeding a threshold value, and to deliver second electrostimulation to the patient in response to the pain score falling below the threshold value. The first and second electrostimulations may differ in at least one of an electrostimulation energy, an electrostimulation pulse shape, or an electrostimulation pattern.

In Example 5, the subject matter of any one or more of Examples 1-4 optionally includes the calibration circuit that may be further configured to establish or update the fusion model using the measurements of the plurality of physiological or functional signals and the reference pain quantification during an induced pain episode.

In Example 6, the subject matter of Example 5 optionally includes the induced pain episode that corresponds to delivery of programmed electrostimulation to a target tissue.

In Example 7, the subject matter of any one or more of Examples 5-6 optionally includes the induced pain episode that corresponds to execution of a stress test.

In Example 8, the subject matter of any one or more of Examples 1-7 optionally includes the reference pain quantification that may comprise a user input of perceived pain scales corresponding to the multiple pain intensities.

In Example 9, the subject matter of any one or more of Examples 1-8 optionally includes the reference pain quantification that may comprise quantified functional scores corresponding to the multiple pain intensities.

In Example 10, the subject matter of any one or more of Examples 1-9 optionally includes the reference pain quantification that may include a plurality of pain scales, and the calibration circuit that may be configured to: compute correlations between the plurality of pain scales and measurements from the plurality of physiological or functional signals corresponding to the plurality of pain scales; and establish or update the fusion model using the computed correlations.

In Example 11, the subject matter of Example 10 optionally includes the pain analyzer circuit that may be configured to generate the pain score using a combination of a plurality of signal metrics weighted by a respective plurality of weight factors. The calibration circuit may be configured to establish or update the fusion model by adjusting the weight factors to be proportional to the computed correlations.

In Example 12, the subject matter of any one or more of Examples 1-11 optionally includes the reference pain quantification that comprises a pain perception curve. The calibration circuit may be configured to: generate psychometric curves using measurements of a plurality of signal metrics of the sensed plurality of physiological or functional signals corresponding to the plurality of pain scales; and establish or update the fusion model based on an alignment metric between the pain perception curve and the generated psychometric curves.

In Example 13, the subject matter of Example 12 optionally includes the pain analyzer circuit that may be configured to generate the pain score using a combination of the plurality of signal metrics weighted by the respective plurality of weight factors. The calibration circuit may be configured to establish or update the fusion model by adjusting the weight factors to be proportional to the alignment metric between the pain perception curve and the generated psychometric curves.

In Example 14, the subject matter of any one or more of Examples 1-13 optionally includes the output unit that may be further configured to produce an alert based on the pain score.

In Example 15, the subject matter of Example 2 optionally includes an implantable neuromodulator device (IND) that includes one or more of the sensor circuit, the pain analyzer circuit, the calibration circuit, or the electrostimulator.

Example 16 is a method for managing pain of a patient using an implantable neuromodulator device (IND). The method comprises steps of: sensing a plurality of physiological or functional signals corresponding to multiple pain intensities from a patient using one or more sensors; generating a reference pain quantification corresponding to the multiple pain intensities; establishing or updating a fusion model based on (1) measurements from the plurality of physiological or functional signals corresponding to the multiple pain intensities and (2) the reference pain quantification corresponding to the multiple pain intensities; generating a pain score using the sensed plurality of the physiological or functional signals and the established or updated fusion model; and outputting the pain score to a user or a process.

In Example 17, the subject matter of Example 16 optionally includes delivering a pain therapy via the IND. The pain therapy may include electrostimulation energy determined according to the pain score.

In Example 18, the subject matter of Example 17 optionally includes delivering a programmed electrostimulation to a target tissue to induce a pain episode with the multiple pain intensities. The fusion model may be established or updated based on the measurements from the plurality of physiological or functional signals during the induced pain episode and the reference pain quantification during the induced pain episode.

In Example 19, the subject matter of Example 16 optionally includes executing a stress test to induce a pain episode with the multiple pain intensities. The fusion model may be established or updated based on the measurements from the plurality of physiological or functional signals during the induced pain episode and the reference pain quantification during the induced pain episode.

In Example 20, the subject matter of Example 16 optionally includes the reference pain quantification that comprises a user input of perceived pain scales corresponding to the multiple pain intensities.

In Example 21, the subject matter of Example 16 optionally includes the reference pain quantification that comprises quantified functional scores corresponding to the multiple pain intensities.

In Example 22, the subject matter of Example 16 optionally includes the reference pain quantification that may include a plurality of pain scales, and the fusion model that may include a combination of a plurality of signal metrics weighted by a respective plurality of weight factors. The establishing or updating the fusion model may further include establishing or updating the weight factors to be proportional to correlations between the plurality of pain scales and measurements from the plurality of physiological or functional signals corresponding to the plurality of pain scales.

In Example 23, the subject matter of Example 16 optionally includes the reference pain quantification that may include a pain perception curve, and the fusion model may include a combination of a plurality of signal metrics weighted by a respective plurality of weight factors. The establishing or updating the fusion model may further include steps of: generating psychometric curves using measurements of a plurality of signal metrics of the sensed plurality of physiological or functional signals corresponding to the plurality of pain scales; and establishing or updating the weight factors to be proportional to alignment metrics between the pain perception curve and the generated psychometric curves.

Systems and methods of sensor-based pain assessment that adapt to changes in patient physiological or functional response to pain, as discussed in this document, may improve automated patient pain characterization, as well as individualized therapies to alleviate pain or to reduce side effects. The systems, devices, and methods discussed in this document may also enhance the performance and functionality of a pain management system or device. A device or a system programmed with the sensor-based pain assessment methods can have improved automaticity in medical diagnostics. More efficient device memory or communication bandwidth usage may be achieved by storing or transmitting medical information more relevant to clinical decisions. Additionally, through improved pain therapy efficacy based on patient individual need, battery longevity of an implantable device may be enhanced, or pain medication volume may be saved.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

Disclosed herein are systems, devices, and methods for or assessing pain in a subject, and programming neurostimulation based on a pain score generated from physiological or functional signals acquired by multiple sensors. In various embodiments, the present system may sense one or more physiological or functional signals, and generate a pain score using the sensed physiological or functional signals and a fusion model. The system may calibrate the fusion model based on measurements from the physiological or functional signals and a reference pain quantification corresponding to multiple pain intensities. The system may include a neurostimulator that controls the delivery of pain therapy by automatically adjusting stimulation parameters based on the pain score generated using the calibrated fusion model.

The present system may be implemented using a combination of hardware and software designed to provide a closed-loop pain management regimen to increase therapeutic efficacy, increase patient satisfaction for neurostimulation therapies, reduce side effects, and/or increase device longevity. The present system may be applied in any neurostimulation (neuromodulation) therapies, including but not limited to SCS, DBS, PNS, FES, motor cortex stimulation, sacral nerve stimulation, and vagus nerve stimulation (VNS) therapies. In various examples, instead of providing closed-loop pain therapies, the systems, devices, and methods described herein may be used to monitor the patient and assess pain that either occurs intrinsically or is induced by nerve block procedures or radiofrequency ablation therapies, or side effects like paresthesia caused by the stimulation therapy, among others. The patient monitoring may include generating recommendations to the patient or a clinician regarding pain treatment.

Figure 1:
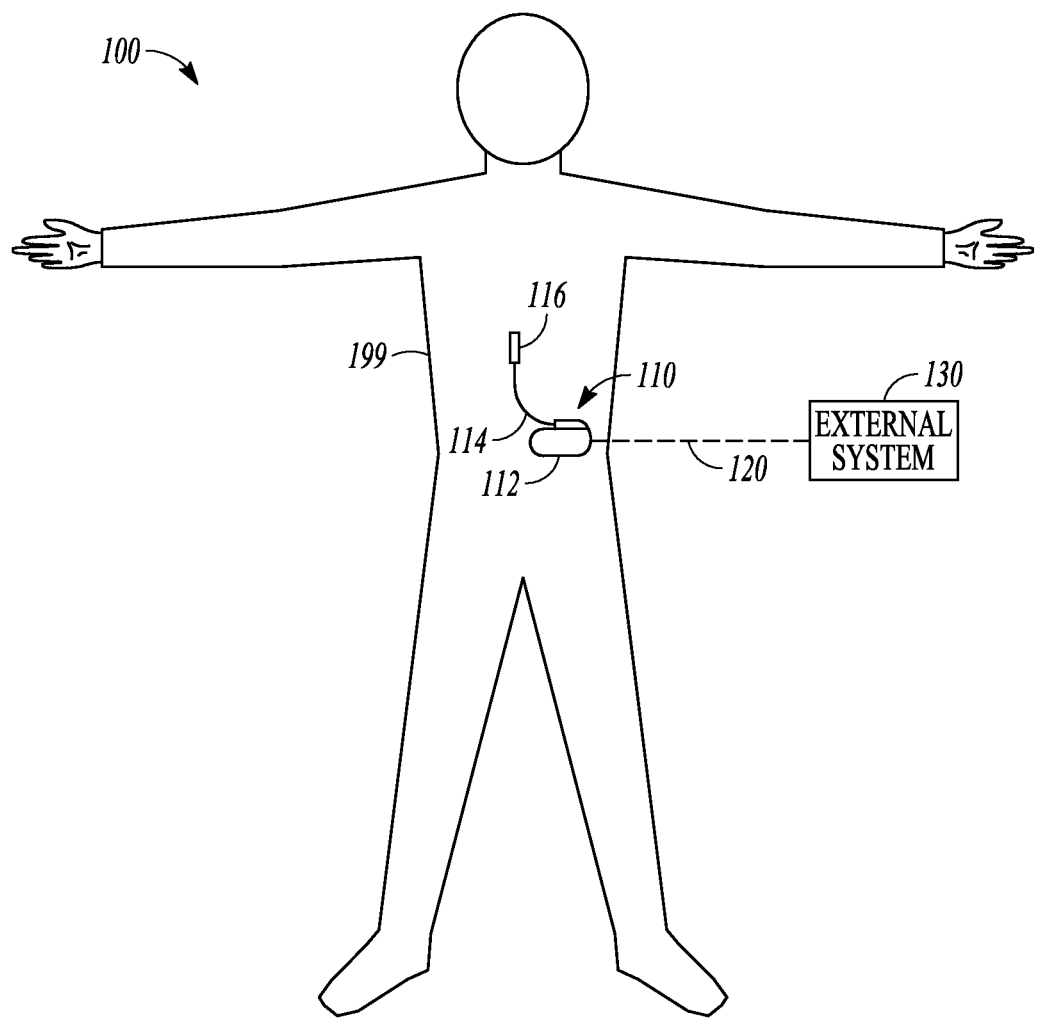
FIG. 1 illustrates, by way of example and not limitation, a neuromodulation system and portions of an environment in which the neuromodulation system may operate.

FIG. 1 illustrates, by way of example and not limitation, a neuromodulation system 100 for managing pain of a subject such as a patient with chronic pain, and portions of an environment in which the neuromodulation system 100 may operate. The neuromodulation system 100 may include an implantable system 110 that may be associated with a body 199 of the subject, and an external system 130 in communication with the implantable system 110 via a communication link 120.

The implantable system 110 may include an ambulatory medical device (AMD), such as an implantable neuromodulator device (IND) 112, a lead system 114, and one or more electrodes 116. The IND 112 may be configured for subcutaneous implant in the chest, abdomen, upper gluteal surface, or other parts of the patient body 199. The IND 112 may be configured as a monitoring and diagnostic device. The IND 112 may include a hermetically sealed can that houses sensing circuitry to sense physiological or functional signals from the patient via sensing electrodes or ambulatory sensors associated with the patient and in communication with the IND 112. In some examples, the sensing electrodes or the ambulatory sensors may be included within the IND 112. The physiological or functional signals, when measured during a pain episode, may be correlative to severity of the pain. The IND 112 may characterize and quantify the pain, such as to determine onset, intensity, severity, duration, or patterns of the pain experienced by the subject. The IND 112 may generate an alert to indicate occurrence of a pain episode, pain exacerbation, or efficacy of pain therapy, and present the alert to a clinician.

The IND 112 may alternatively be configured as a therapeutic device for treating or alleviating the pain. In addition to the pain monitoring circuitry, the IND 112 may further include a therapy unit that can generate and deliver energy or modulation agents to a target tissue. The energy may include electrical, magnetic, thermal, or other types of energy. In some examples, the IND 112 may include a drug delivery system such as a drug infusion pump that can deliver pain medication to the patient, such as morphine sulfate or ziconotide, among others.

The IND 112 may include electrostimulation circuitry that generates electrostimulation pulses to stimulate a neural target via the electrodes 116 operably connected to the IND 112. In an example, the electrodes 116 may be positioned on or near a spinal cord, and the electrostimulation circuitry may be configured to deliver SCS to treat pain. In another example, the electrodes 116 may be surgically placed at other neural targets such as a brain or a peripheral neutral tissue, and the electrostimulation circuitry may be configured to deliver brain or peripheral stimulations. Examples of electrostimulation may include deep brain stimulation (DBS), trigeminal nerve stimulation, occipital nerve stimulation, vagus nerve stimulation (VNS), sacral nerve stimulation, sphenopalatine ganglion stimulation, sympathetic nerve modulation, adrenal gland modulation, baroreceptor stimulation, or transcranial magnetic stimulation, spinal cord stimulation (SCS), dorsal root ganglia (DRG) stimulation, motor cortex stimulation (MCS), transcranial direct current stimulation (tDCS), transcutaneous spinal direct current stimulation (tsDCS), pudendal nerve stimulation, multifidus muscle stimulation, transcutaneous electrical nerve stimulation (TENS), tibial nerve stimulation, among other peripheral nerve or organ stimulation. The IND 112 may additionally or alternatively provide therapies such as radiofrequency ablation (RFA), pulsed radiofrequency ablation, ultrasound therapy, high-intensity focused ultrasound (HIFU), optical stimulation, optogenetic therapy, magnetic stimulation, other peripheral tissue stimulation therapies, other peripheral tissue denervation therapies, or nerve blocks or injections.

In various examples, the electrodes 116 may be distributed in one or more leads of the lead system 114 electrically coupled to the IND 112. In an example, the lead system 114 may include a directional lead that includes at least some segmented electrodes circumferentially disposed about the directional lead. Two or more segmented electrodes may be distributed along a circumference of the lead. The actual number and shape of leads and electrodes may vary according to the intended application. Detailed description of construction and method of manufacturing percutaneous stimulation leads are disclosed in U.S. Pat. No. 8,019,439, entitled "Lead Assembly and Method of Making Same," and U.S. Pat. No. 7,650,184, entitled "Cylindrical Multi-Contact Electrode Lead for Neural Stimulation and Method of Making Same," the disclosures of which are incorporated herein by reference. The electrodes 116 may provide an electrically conductive contact providing for an electrical interface between the IND 112 and tissue of the patient. The neurostimulation pulses are each delivered from the IND 112 through a set of electrodes selected from the electrodes 116. In various examples, the neurostimulation pulses may include one or more individually defined pulses, and the set of electrodes may be individually definable by the user for each of the individually defined pulses.

Although the discussion herein with regard to the neuromodulation system 100 focuses on an implantable device such as the IND 112, this is meant only by way of example and not limitation. It is within the contemplation of the present inventors and within the scope of this document that the systems, devices, and methods discussed herein may also be used for pain management via subcutaneous medical devices, wearable medical devices (e.g., wrist watch, patches, garment- or shoe-mounted device), or other external medical devices, or a combination of implantable, wearable, or other external devices. The therapy, such as electrostimulation or medical therapies, may be used to treat various neurological disorders other than pain, which by way of example and not limitation may include epilepsy, migraine, Tourette's syndrome, obsessive compulsive disorder, tremor, Parkinson's disease, or dystonia, among other movement and affective disorders.

The external system 130 may be communicated with the IND 112 via a communication link 120. The external system 130 may include a dedicated hardware/software system such as a programmer, a remote server-based patient management system, or alternatively a system defined predominantly by software running on a standard personal computer. In some examples, at least a portion of the external system 130 may be ambulatory such as configured to be worn or carried by a subject. The external system 130 may be configured to control the operation of the IND 112, such as to program the IND 112 for delivering neuromodulation therapy. The external system 130 may additionally receive via the communication link 120 information acquired by IND 112, such as one or more physiological or functional signals. In an example, the external system 130 may generate a pain score using the physiological or functional signals received from the IND 112 and a fusion model. The external system 130 may program the IND 112 to deliver pain therapy in a closed-loop fashion based on the pain score. In some examples, the external system 130 may update the fusion model such as to adapt to the changes in patient physiological or functional response to pain. Examples of the external system and neurostimulation based on pain score are discussed below, such as with reference to FIGS. 2-3.

The communication link 120 may include one or more communication channels and intermediate devices between the external system and the IND, such as a wired link, a telecommunication link such as an internet connection, or a wireless link such as one or more of an inductive telemetry link, a radio-frequency telemetry link. The communication link 120 may provide for data transmission between the IND 112 and the external system 130. The transmitted data may include, for example, real-time physiological or functional signals acquired by and stored in the IND 112, therapy history data, data indicating device operational status of the IND 112, one or more programming instructions to the IND 112 which may include configurations for sensing physiologic signal or stimulation commands and stimulation parameters, or device self-diagnostic test, among others. In some examples, the IND 112 may be coupled to the external system 130 further via an intermediate control device, such as a handheld external remote control device to remotely instruct the IND 112 to generate electrical stimulation pulses in accordance with selected stimulation parameters produced by the external system 130, or to store the collected data into the external system 130.

Portions of the IND 112 or the external system 130 may be implemented using hardware, software, firmware, or combinations thereof. Portions of the IND 112 or the external system 130 may be implemented using an application-specific circuit that may be constructed or configured to perform one or more particular functions, or may be implemented using a general-purpose circuit that may be programmed or otherwise configured to perform one or more particular functions. Such a general-purpose circuit may include a microprocessor or a portion thereof, a microcontroller or a portion thereof, or a programmable logic circuit, or a portion thereof. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals.

Figure 2:
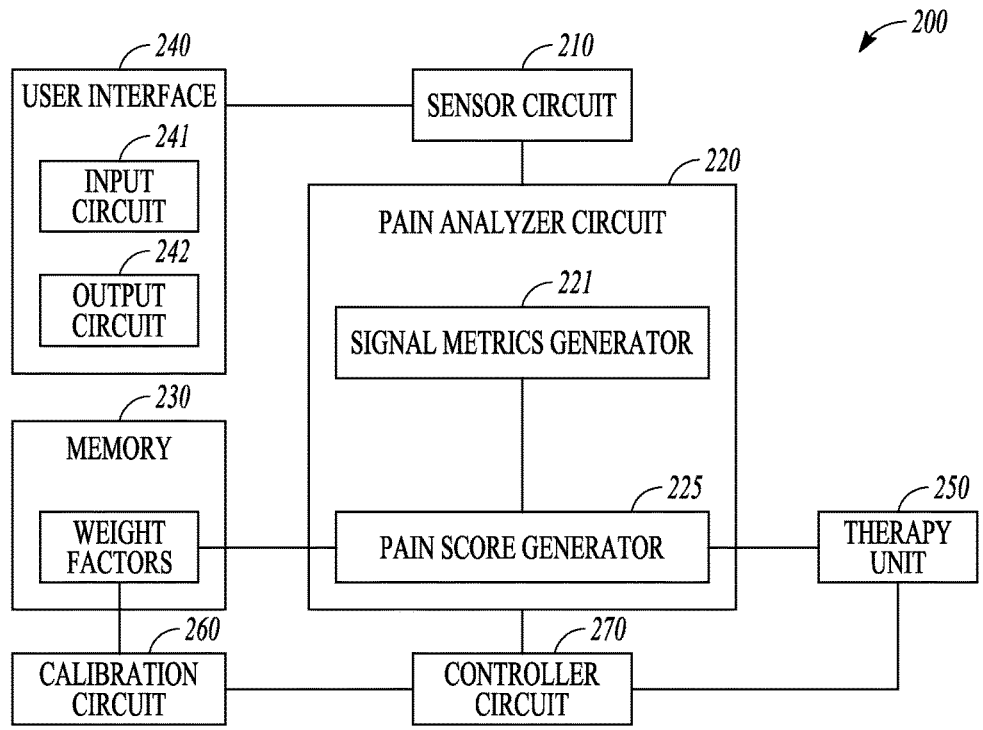
FIG. 2 illustrates, by way of example and not limitation, a block diagram of a pain management system.

FIG. 2 illustrates, by way of example and not limitation, a block diagram of a pain management system 200, which may be an embodiment of the neuromodulation system 100. The pain management system 200 may include a sensor circuit 210, a pain analyzer circuit 220, a memory 230, a user interface 240, a therapy unit 250, a calibration circuit 260, and a controller circuit 270. The pain management system 200 may be configured to assess patient pain using physiological or functional signals sensed using the sensor circuit 210 and a fusion model stored in the memory 230.

The sensor circuit 210 may be coupled to electrodes or various types of ambulatory sensors associated with the patient to sense one or more physiological signals from the patient. The sensor circuit 210 may include sense amplifier circuit that may pre-process the sensed physiological or functional signals, including, for example, amplification, digitization, filtering, or other signal conditioning operations. Various physiological signals, such as cardiac, pulmonary, neural, or biochemical signals may demonstrate characteristic signal properties in response to an onset, intensity, severity, duration, or patterns of pain. In an example, the sensor circuit 210 may be coupled to implantable or wearable sensors to sense cardiac signals such as electrocardiograph (ECG), intracardiac electrogram, gyrocardiography, magnetocardiography, heart rate signal, heart rate variability signal, cardiovascular pressure signal, or heart sounds signal, among others. In another example, the sensor circuit 210 may sense pulmonary signals such as a respiratory signal, a thoracic impedance signal, or a respiratory sounds signal. The sensor circuit 210 may additionally or alternatively be coupled to at least one motion sensor to sense one or more functional signals. The functional signal represent patient motor activities and physical state. Examples of the functional signals may include patient posture, gait, balance, or physical activity signals, among others. Examples of the motion sensor may include an accelerometer, gyroscope (which may be a one-, two-, or three-axis gyroscope), magnetometer (e.g., a compass), inclinometers, goniometers, electromagnetic tracking system (ETS), or a global positioning system (GPS) sensor, among others. Detailed description of functional signals for use in pain characterization are disclosed in commonly assigned U.S. Provisional Patent Application Ser. No. 62/445,075, entitled "PAIN MANAGEMENT BASED ON FUNCTIONAL MEASUREMENTS", the disclosures of which are incorporated herein by reference. Commonly assigned U.S. Provisional Patent Application Ser. No. 62/445,053, entitled "PAIN MANAGEMENT BASED ON CARDIOVASCULAR PARAMETERS" describes cardiovascular parameters such as arterial pulsatile activity and electrocardiography for use in pain analysis, the disclosure of which is incorporated herein by reference in its entirety. Commonly assigned U.S. Provisional Patent Application Ser. No. 62/445,061, entitled "PAIN MANAGEMENT BASED ON BRAIN ACTIVITY MONITORING" describes information of brain activity for use in pain analysis, the disclosure of which is incorporated herein by reference in its entirety. Commonly assigned U.S. Provisional Patent Application Ser. No. 62/445,061, entitled "PAIN MANAGEMENT BASED ON BRAIN ACTIVITY MONITORING" describes information of brain activity for use in pain analysis, the disclosure of which is incorporated herein by reference in its entirety. Commonly assigned U.S. Provisional Patent Application Ser. No. 62/445,069, entitled "PAIN MANAGEMENT BASED ON RESPIRATION-MEDIATED HEART RATES" describes information of respiration-mediated heart rate for use in pain analysis, the disclosure of which is incorporated herein by reference in its entirety. Commonly assigned U.S. Provisional Patent Application Ser. No. 62/445,082, entitled "PAIN MANAGEMENT BASED ON EMOTIONAL EXPRESSION MEA- SUREMENTS" describes measurements of patient emotional expressions for use in pain analysis, the disclosure of which is incorporated herein by reference in its entirety. Commonly assigned U.S. Provisional Patent Application Ser. No. 62/445,092, entitled "PAIN MANAGEMENT BASED ON MUSCLE PENSION MEASUREMENTS" describes measurements of patient muscle tension including electromyography for use in pain analysis, the disclosure of which is incorporated herein by reference in its entirety. One or more of these additional signals or measurements may be used by the pain analyzer circuit 220 to generate a pain score.

In some examples, the sensor circuit 210 may sense biochemical signals such as blood chemistry measurements or expression levels of one or more biomarkers, which may include, by way of example and not limitation, B-type natriuretic peptide (BNP) or N-terminal pro b-type natriuretic peptide (NT-proBNP), serum cytokine profiles, P2X4 receptor expression levels, gamma-aminobutyric acid (GABA) levels, TNFα and other inflammatory markers, cortisol, adenosine, Glial cell-derived neurotrophic factor (GDNF), Nav 1.3, Nav 1.7, or Tetrahydrobiopterin (BH4) levels, among other biomarkers.

The pain analyzer circuit 220 may generate a pain score using at least the physiological or functional signals received from the sensor circuit 210. The pain analyzer circuit 220 may be implemented as a part of a microprocessor circuit, which may be a dedicated processor such as a digital signal processor, application specific integrated circuit (ASIC), microprocessor, or other type of processor for processing information including physical activity information. Alternatively, the microprocessor circuit may be a general purpose processor that may receive and execute a set of instructions of performing the functions, methods, or techniques described herein.

The pain analyzer circuit 220 may include circuit sets comprising one or more other circuits or sub-circuits that may, alone or in combination, perform the functions, methods or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

As illustrated in FIG. 2, the pain analyzer circuit 220 may include a signal metrics generator 221 and a pain score generator 225. The signal metrics generator 221 may generate one or more signal metrics from the sensed at least one physiological or functional signal. The signal metrics may include statistical parameters extracted from the sensed signal, such as signal mean, median, or other central tendency measures or a histogram of the signal intensity, among others. The signal metrics may additionally or alternatively include morphological parameters such as maximum or minimum within a specific time period such as a cardiac cycle, positive or negative slope or higher order statistics, or signal power spectral density at a specific frequency range, among other morphological parameters. The signal metrics may additionally include timing information such as a time interval between a first characteristic point in one signal and a second characteristic point in another signal.

The pain score generator 225 may generate a pain score using the measurements of the signal metrics, such as generated by the signal metrics generator 221, and a fusion model stored in the memory 230. The pain score can be represented as a numerical or categorical value that quantifies the patient overall pain symptom. The fusion model may involve instructions for combining the measurements of the signal metrics using a specific algorithm. Examples of the fusion algorithms may include weighted averages, voting, decision trees, or neural networks, among other linear or nonlinear algorithms. In an example, the fusion model may include weighted combination of the signal metrics weighted by their respective weight factors. The combination can be linear or nonlinear. The pain score generator 225 may compare the composite signal metric to one or more threshold values or range values, and assign a corresponding pain score (such as numerical values from 0 to 10) based on the comparison.

In another example, the pain score generator 225 may compare the signal metrics to their respective threshold values or range values, assign corresponding signal metric-specific pain scores based on the comparison, and compute a composite pain score using a linear or nonlinear fusion of the signal metric-specific pain scores weighted by their respective weight factors. In an example, the threshold can be inversely proportional to signal metric's sensitivity to pain. A signal metric that is more sensitive to pain may have a corresponding lower threshold and a larger metric-specific pain score, thus plays a more dominant role in the composite pain score than another signal metric that is less sensitive to pain. Examples of the fusion algorithm may include weighted averages, voting, decision trees, or neural networks, among others. The pain score generated by the pain score generator 225 may be output to a system user or a process.

The memory 230 may be configured to store sensor signals, signal metrics, and the pain scores such as generated by the pain score generator 225. Data may be stored at the memory 230 continuously, periodically, or in a commanded mode such as triggered by a user instruction or a specific event. As illustrated in FIG. 2, the memory 230 may store the fusion model for computing the composite pain score. The fusion model may be provided by a system user, or may alternatively be automatically established or updated such as based on the corresponding signal metrics reliability in representing pain intensity. Examples of the automatic update of fusion model are discussed below, such as with reference to FIGS. 3 and 4.

The user interface 240 may include an input circuit 241 and an output unit 242. In an example, at least a portion of the user interface 240 may be implemented in the external system 130. The input circuit 241 may enable a system user to program the parameters used for sensing the physiological or functional signals, generating signal metrics, and generating the pain score. The input circuit 241 may be coupled to one or more input devices such as a keyboard, on-screen keyboard, mouse, trackball, touchpad, touch-screen, or other pointing or navigating devices. In some example, the input device may be incorporated in a mobile device such as a smart phone or other portable electronic device that can execute a mobile application ("App"). The mobile App may enable a patient to provide pain description or quantified pain scales during the pain episodes. In an example, the input circuit 241 may enable a user to confirm, reject, or edit the programming of the therapy unit 250, such as parameters associated with electrostimulation, as to be discussed as follows.

The output unit 242 may include a display to present to a system user the pain score. The output unit 242 may also display information including the physiological or functional signals, trends of the signal metric, or any intermediary results for pain score calculation such as the signal metric-specific pain scores. The information may be presented in a table, a chart, a diagram, or any other types of textual, tabular, or graphical presentation formats, for displaying to a system user. The presentation of the output information may include audio or other human-perceptible media format. In an example, the output unit 242 may generate alerts, alarms, emergency calls, or other forms of warnings to signal the system user about the pain score.

The therapy circuit 250 may be configured to deliver a therapy to the patient based on the pain score generated by the pain score generator 225. The therapy circuit 250 may include an electrostimulator configured to generate electrostimulation energy to treat pain. In an example, the electrostimulator may deliver spinal cord stimulation (SCS) via electrodes electrically coupled to the electrostimulator. The electrodes may be surgically placed at a region at or near a spinal cord tissue, which may include, by way of example and not limitation, dorsal column, dorsal horn, spinal nerve roots such as the dorsal nerve root, dorsal root entry zone, spinothalamic tract, and dorsal root ganglia. The SCS may be in a form of stimulation pulses that are characterized by pulse amplitude, pulse width, stimulation frequency, duration, on-off cycle, pulse shape or waveform, temporal pattern of the stimulation, among other stimulation parameters. Examples of the stimulation pattern may include burst stimulation with substantially identical inter-pulse intervals, or ramp stimulation with incremental inter-pulse intervals or with decremental inter-pulse intervals. In some examples, the frequency or the pulse width may change from pulse to pulse. The electrostimulator may additionally or alternatively deliver electrostimulation to other target tissues such as brain or peripheral nerves tissues. In an example, the electrostimulator may deliver transcutaneous electrical nerve stimulation (TENS) via detachable electrodes that are affixed to the skin.

The therapy circuit 250 may additionally or alternatively include a drug delivery system, such as an intrathecal drug delivery pump that may be surgically placed under the skin, and programmed to inject medication or biologics through a catheter to an area around the spinal cord. Other examples of drug delivery system may include a computerized patient-controlled analgesia pump that may deliver the prescribed pain medication to the patient such as via an intravenous line. In some examples, the therapy circuit 250 may be delivered according to the pain score received from the pain score generator 225.

The calibration circuit 260 may be configured to establish or update a fusion model based on measurements from the plurality of physiological or functional signals corresponding to multiple pain intensities and a reference pain quantification corresponding to the multiple pain intensities. The reference pain quantification may be generated from patient spontaneous pain episodes, or one or more induced pain episodes in a pain assessment session. The controller circuit 270 may control the calibration circuit 260 to establish or update the fusion model, such as according to a user programming instruction, or automatically triggered by a specific event such as a change of patient health status or daily routine as detected by a sensor. The controller circuit 270 may additionally control the pain analyzer circuit 220 to generate a pain score using the established or updated fusion model. The controller circuit 270 may also be coupled to the therapy unit 250 to control the therapy delivery such as electrostimulation energy according to the pain score. Examples of the calibration of fusion models are discussed below, such as with reference to FIGS. 4A-B.

Figure 3:
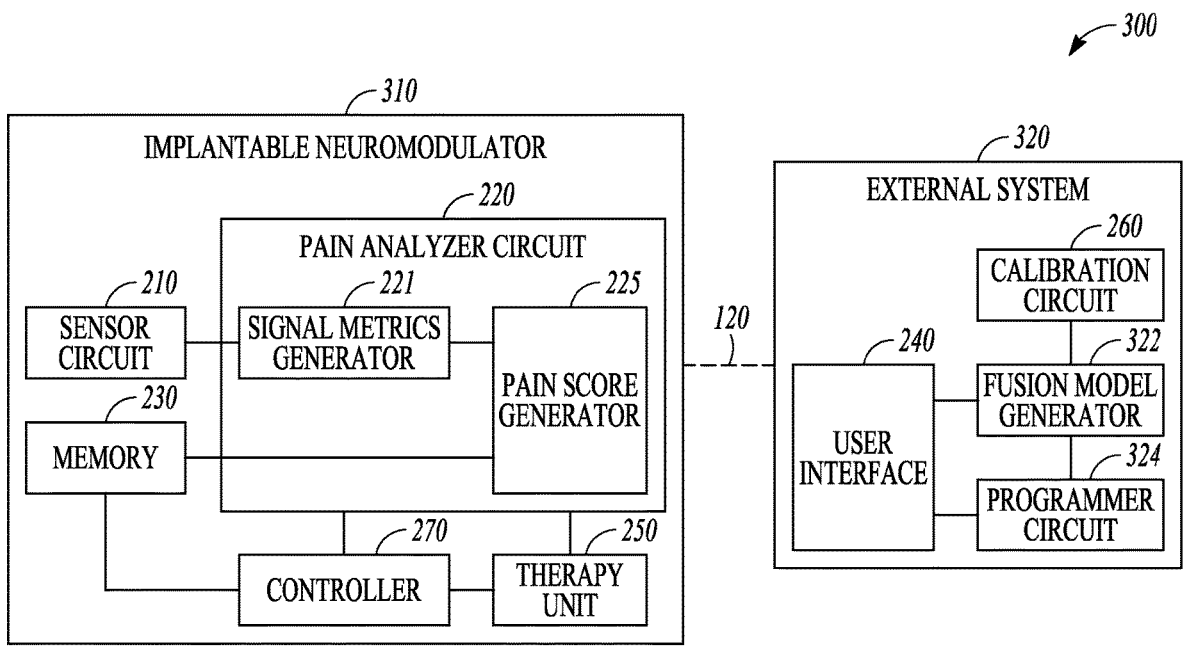
FIG. 3 illustrates, by way of example and not limitation, a block diagram of a pain management system comprising an implantable neuromodulator.

FIG. 3 illustrates, by way of example and not limitation, a block diagram of another example of a pain management system 300, which may be an embodiment of the neuromodulation system 100 or the pain management system 200. The pain management system 300 may include an implantable neuromodulator 310 and an external system 320, which may be, respectively, embodiments of the IND 112 and the external system 130 as illustrated in FIG. 1. The external system 320 may be communicatively coupled to the implantable neuromodulator 310 via the communication link 120.

The implantable neuromodulator 310 may include several components of the pain management system 200 as illustrated in FIG. 2, including the sensor circuit 210, the pain analyzer circuit 220, the memory 230, and the therapy unit 250. As discussed with reference to FIG. 2, the pain analyzer circuit 220 includes the pain score generator 225 that determine a pain score using weight factors stored in the memory 230 and the signal metrics from the signal metrics generator 221 which may also be included in the pain analyzer circuit 220. In some examples, a portion or the entirety of the pain analyzer 231 may alternatively be included in the external system 320, or be distributed between the implantable neuromodulator 310 and the external system 320.

The controller circuit 270 may control the generation of electrostimulation pulses according to specific stimulation parameters. The stimulation parameters may be provided by a system user. Alternatively, the stimulation parameters may be automatically determined based on the intensity, severity, duration, or pattern of pain, which may be subjectively described by the patient or automatically quantified based on the physiological or functional signals sensed by the sensor circuit 210. For example, when a patient-described or sensor-indicated quantification exceeds a respective threshold value or falls within a specific range indicating elevated pain, the electrostimulation energy may be increased to provide stronger pain relief. Increased electrostimulation energy may be achieved by programming a higher pulse intensity, a higher frequency, or a longer stimulation duration or "on" cycle, among others. Conversely, when a patient-described or sensor-indicated pain quantification falls below a respective threshold value or falls within a specific range indicating no pain or mild pain, the electrostimulation energy may be decreased. The controller circuit 270 may also adjust stimulation parameters to alleviate side effects introduced by the electrostimulation of the target tissue.

Additionally or alternatively, the controller circuit 270 may control the therapy unit 250 to deliver electrostimulation pulses via specific electrodes. In an example of pain management via SCS, a plurality of segmented electrodes, such as the electrodes 116, may be distributed in one or more leads. The controller circuit 270 may configure the therapy unit 250 to deliver electrostimulation pulses via a set of electrodes selected from the plurality of electrodes. The electrodes may be manually selected by a system user or automatically selected based on the pain score.

The implantable neuromodulator 310 may receive the information about electrostimulation parameters and the electrode configuration from the external system 320 via the communication link 120. Additional parameters associated with operation of the therapy unit 250, such as battery status, lead impedance and integrity, or device diagnostic of the implantable neuromodulator 310, may be transmitted to the external system 320. The controller circuit 270 may control the generation and delivery of electrostimulation using the information about electrostimulation parameters and the electrode configuration from the external system 320. Examples of the electrostimulation parameters and electrode configuration may include: temporal modulation parameters such as pulse amplitude, pulse width, pulse rate, or burst intensity; morphological modulation parameters respectively defining one or more portions of stimulation waveform morphology such as amplitude of different phases or pulses included in a stimulation burst; or spatial modulation parameters such as selection of active electrodes, electrode combinations which define the electrodes that are activated as anodes (positive), cathodes (negative), and turned off (zero), and stimulation energy fractionalization which defines amount of current, voltage, or energy assigned to each active electrode and thereby determines spatial distribution of the modulation field.

In an example, the controller circuit 270 may control the generation and delivery of electrostimulation in a closed-loop fashion by adaptively adjusting one or more stimulation parameters or stimulation electrode configuration based on the pain score. For example, if the score exceeds the pain threshold (or falls within a specific range indicating an elevated pain), then the first electrostimulation may be delivered. Conversely, if the composite pain score falls below a respective threshold value (or falls within a specific range indicating no pain or mild pain), then a second pain therapy, such as second electrostimulation may be delivered. The first and second electrostimulations may differ in at least one of the stimulation energy, pulse amplitude, pulse width, stimulation frequency, duration, on-off cycle, pulse shape or waveform, electrostimulation pattern such as electrode configuration or energy fractionalization among active electrodes, among other stimulation parameters. In an example, the first electrostimulation may have higher energy than the second electrostimulation, such as to provide stronger effect of pain relief. Examples of increased electrostimulation energy may include a higher pulse intensity, a higher frequency, or a longer stimulation duration or "on" cycle, among others.

The parameter adjustment or stimulation electrode configuration may be executed continuously, periodically at specific time, duration, or frequency, or in a commanded mode upon receiving from a system user a command or confirmation of parameter adjustment. In some examples, the closed-loop control of the electrostimulation may be further based on the type of the pain, such as chronic or acute pain. In an example, the pain analyzer circuit 220 may trend the signal metric over time to compute an indication of abruptness of change of the signal metrics, such as a rate of change over a specific time period. The pain episode may be characterized as acute pain if the signal metric changes abruptly (e.g., the rate of change of the signal metric exceeding a threshold), or as chronic pain if the signal metric changes gradually (e.g., the rate of change of the signal metric falling below a threshold). The controller circuit 270 may control the therapy unit 250 to deliver, withhold, or otherwise modify the pain therapy in accordance with the pain type. For example, incidents such as toe stubbing or bodily injuries may cause abrupt changes in certain signal metrics, but no adjustment of the closed-loop pain therapy is deemed necessary. On the contrary, if the pain analyzer circuit 220 detects chronic pain characterized by gradual signal metric change, then the closed-loop pain therapy may be delivered accordingly.

The external system 320 may include the user interface 240, the calibration circuit 260, a fusion model generator 322, and a programmer circuit 324. The fusion model generator 322 may generate a fusion model used by the pain score generator 225 to generate the pain score. In an example, the fusion model may include a combination of signal metrics weighted by their respective weight factors indicating the signal metrics' reliability in representing pain intensity. A sensor metric that is more reliable, or more sensitive or specific to the pain, would be assigned a larger weight than another sensor metric that is less reliable, or less sensitive or specific to the pain. The calibration circuit 260 may update the fusion model using measurements signal metrics corresponding to multiple pain intensities and a reference pain quantification corresponding to the multiple pain intensities, as to be discussed below with reference to FIGS. 4A-B.

The programmer circuit 324 may produce parameter values for operating the implantable neuromodulator 310, including parameters for sensing physiological or functional signals and generating signal metrics, and parameters or electrode configurations for electrostimulation. In an example, the programmer circuit 324 may generate the stimulation parameters or electrode configurations for SCS based on the pain score produced by the pain score generator 225. Through the communication link 120, the programmer circuit 324 may continuously or periodically provide adjusted stimulation parameters or electrode configuration to the implantable neuromodulator 210. By way of non-limiting example and as illustrated in FIG. 3, the programmer circuit 324 may be coupled to the user interface 234 to allow a user to confirm, reject, or edit the stimulation parameters, sensing parameters, or other parameters controlling the operation of the implantable neuromodulator 210. The programmer circuit 324 may also adjust the stimulation parameter or electrode configuration in a commanded mode upon receiving from a system user a command or confirmation of parameter adjustment.

The programmer circuit 324, which may be coupled to the fusion model generator 322, may initiate a transmission of the weight factors generated by the fusion model generator 322 to the implantable neuromodulator 310, and store the weight factors in the memory 230. In an example, the weight factors received from the external system 320 may be compared to previously stored weight factors in the memory 230. The controller circuit 270 may update the weight factors stored in the memory 230 if the received weight factors are different than the stored weights. The pain analyzer circuit 220 may use the updated weight factors to generate a pain score. In an example, the update of the stored weight factors may be performed continuously, periodically, or in a commanded mode upon receiving a command from a user.

In some examples, the pain score may be used by a therapy unit (such as an electrostimulator) separated from the pain management system 300. In various examples, the pain management system 300 may be configured as a monitoring system for pain characterization and quantification without delivering closed-loop electrostimulation or other modalities of pain therapy. The pain characterization and quantification may be provided to a system user such as the patient or a clinician, or to a process including, for example, an instance of a computer program executable in a microprocessor. In an example, the process includes computer-implemented generation of recommendations or an alert to the system user regarding pain medication (e.g., medication dosage and time for taking a dose), electrostimulation therapy, or other pain management regimes. The therapy recommendations or alert may be based on the pain score, and may be presented to the patient or the clinician in various settings including in-office assessments (e.g. spinal cord stimulation programming optimization), in-hospital monitoring (e.g. opioid dosing during surgery), or ambulatory monitoring (e.g. pharmaceutical dosing recommendations).

In an example, in response to the pain score exceeding a threshold which indicates elevated pain symptom, an alert may be generated and presented at the user interface 240 to remind the patient to take pain medication. In another example, therapy recommendations or alerts may be based on information about wearing-off effect of pain medication, which may be stored in the memory 230 or received from the user interface 240. When the drug effect has worn off, an alert may be generated to remind the patient to take another dose or to request a clinician review of the pain prescription. In yet another example, before a pain therapy such as neurostimulation therapy is adjusted (such as based on the pain score) and delivered to the patient, an alert may be generated to forewarn the patient or the clinician of any impending adverse events. This may be useful as some pain medication may have fatal or debilitating side effects. In some examples, the pain management system 300 may identify effect of pain medication addiction such as based on physiological or functional signals. An alert may be generated to warn the patient about effects of medication addiction and thus allow medical intervention.

In some examples, the pain analyzer circuit 220 may be alternatively included in the external system 320. The pain analyzer circuit 220, or a portion of the pain analyzer circuit 220 such as the signal metrics generator 221 or the pain score generator 225, may be included in a wearable device configured to be worn or carried by a subject. At least a portion of the sensor circuit 210 may also be included in the external system 320. A clinician may use the external system 320 to program the implantable neuromodulator 310 with appropriate pain therapy based on the pain score generated at the external system 320, such as during a clinical trial or patient follow-up visit at the clinic.

Figure 4A:
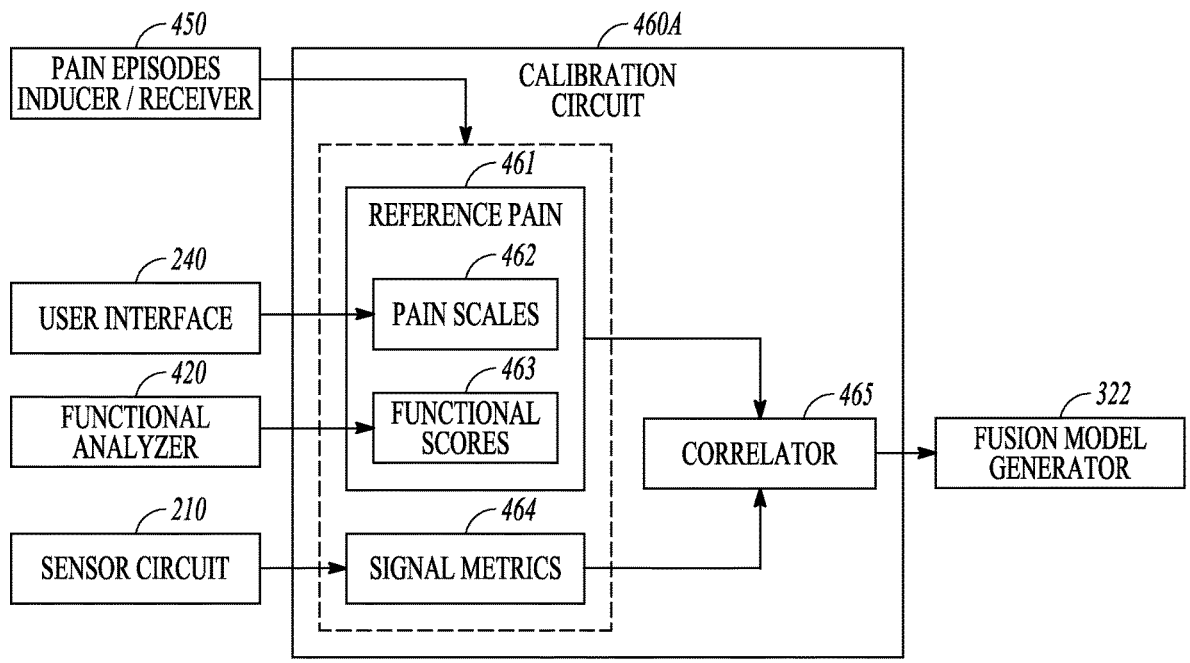
FIGS. 4A-B illustrate, by way of example and not limitation, block diagrams of portions of a pain management system for establishing or updating a fusion model used for generating a composite pain score.
Figure 4B:
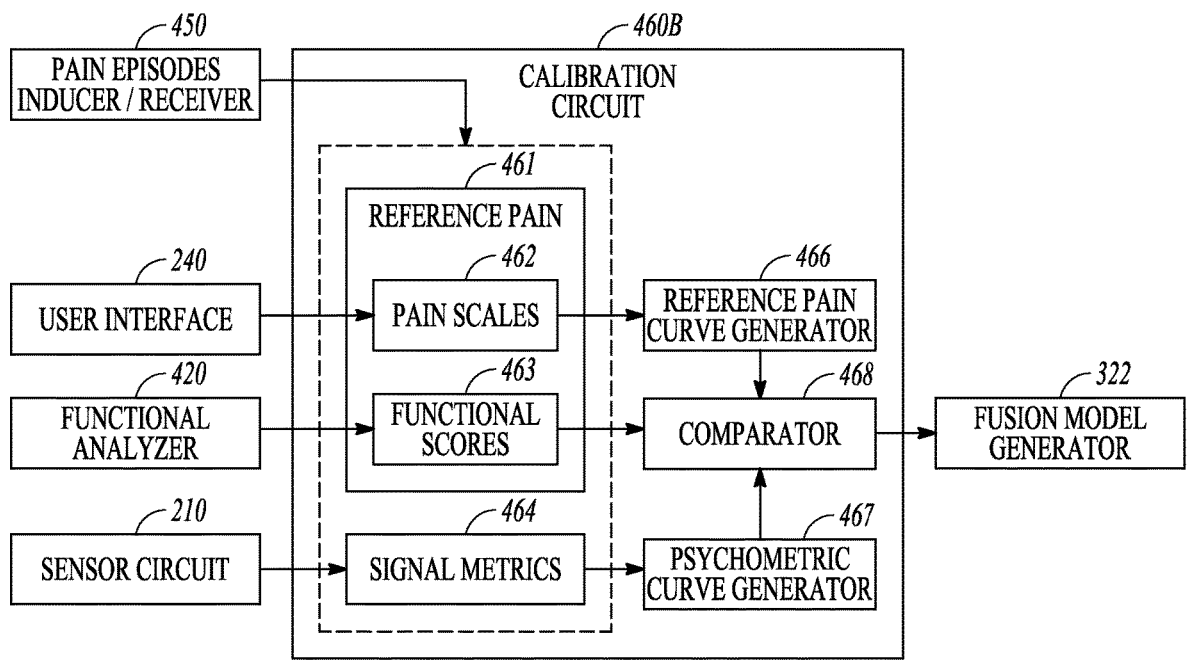

FIGS. 4A-B illustrate, by way of example and not limitation, block diagrams of portions of a pain management system for establishing or updating a fusion model used for generating a composite pain score. The system portions in FIGS. 4A-B include respective calibration circuits 460A-B, which may be embodiments of the calibration circuit 260. The calibration circuits 460A-B may each be coupled to a sensor circuit 210, and one or both of the user interface 240 or a functional analyzer 420. During one or more pain episodes that involve multiple levels of pain intensities, the calibration circuits 460A-B may each determine a reference pain quantification corresponding to the multiple pain intensities using one or both of the user interface 240 or a functional analyzer 420, sense a plurality of physiological or functional signals corresponding to the multiple pain intensities using the sensor circuit 210, and calibrate the fusion model such as based on a comparison of the reference pain quantification and the plurality of physiological or functional signals.

As illustrated in each of FIGS. 4A-B, the calibration circuit may be coupled to a pain episodes inducer/receiver 450 that may receive spontaneous pain episodes or induce pain episodes. The spontaneous pain episodes may occur in an ambulatory setting in patient daily life. Upon an onset of a spontaneous pain episode, the sensor circuit 210 may record a plurality of physiological or functional signals, automatically or activated at least partially by the patient. The induced pain episodes may be produced in a pain assessment session administered by a clinician. An external stimulator or an implantable stimulator (such as the implantable neuromodulator 310) may be programmed, such as by a clinician during a patient follow-up, to execute a pain assessment protocol that includes different levels of stimulation energy. The different stimulation energy levels may be achieved by adjusting the pulse intensity, duration, frequency, on/off period, or electrode selection and stimulation vector configuration, among other therapy parameters. The pain assessment session may include a low stimulation energy level such as by temporarily withholding delivery of pain-relief electrostimulation, a high stimulation energy level such as by delivering the maximal tolerable and safe pain-relief stimulation prescribed by the clinician, or one or more intermediate stimulation energy levels between the minimal and maximal energy levels to achieve intermediate levels of pain reduction effect. Electrostimulation with different levels of stimulation energy may result in different pain intensities. Additionally or alternatively, the pain assessment protocol may include pressure stimulation, thermal stimulation (e.g., hot or cold stimulation applied to patient skin), or other peripheral somatosensory stimulation. In some examples, the pain assessment protocol may include non-pain related tasks, such as stress, leg lift, or grip test. The sensor circuit 210 may record a plurality of physiological or functional signals during the pain assessment session.

The signal metrics generator 221 may generate, from the plurality of physiological or functional signals sensed during the spontaneous or induced pain episodes, a set of signal metrics $\{X\}$. For multiple spontaneous or induced pain episodes with multiple such as a total of n pain intensities (P1, P2, . . . , Pn), the signal metrics generator 221 may generate corresponding multiple sets of signal metrics 464 ($\{X1\}, \{X2\}, \ldots, \{Xn\}$), where each signal metric set $\{Xi\}=\{Xi(1), Xi(2), \ldots, Xi(m)\}$ represents m signal metrics corresponding to the spontaneous or induced pain episode with pain intensity level of Pi. Also during the spontaneous or induced pain episodes, the patient may provide, via the user interface 240, self-reported perceived pain scales 462, denoted by (rP1, rP2, . . . , rPn) that correspond to the n pain intensities. The patient self-reported perceived pain scales (rP1, rP2, . . . , rPn) may take numerical or categorical values, and represent a reference pain quantification corresponding to the multiple pain intensities.

The functional analyzer 420 may alternatively or additionally perform quantified functional assessment of the patient, and generate functional scores 463, denoted by (F1, F2, . . . , Fn), that correspond to the multiple pain intensities during the spontaneous or induced pain episodes. The functional scores 463 represent patient motion control functionality such as a posture, a gait, a balance while in locomotion, a locomotion pattern, or a physical activity level. The functional scores 463 may be generated when the patient undergoes a standard functional assessment test, such as one or more of a gait analysis procedure, a six-minute walk test, or a timed up-and-go test, among other standardized functional tests. The gait analysis procedure evaluates a patient endurance or fatigue during locomotion. The six-minute walk test measures the distance an individual is able to walk over a total of six minutes on a hard, flat surface, and is an indicator of a patient functional exercise capacity. The timed up-and-go test measures the time that a person takes to rise from a chair, walk three meters, turn around, walk back to the chair, and sit down, and is an indicator of a patient mobility.

The functional scores (F1, F2, . . . , Fn) may be indicative of various levels of pain intensities. For example, with elevated pain, the patient may present with significantly unbalanced posture and abnormal gait or locomotion patterns, shorter six-minute walk distance, or longer time for completion of the timed up-and-go test. The functional scores (F1, F2, . . . , Fn) represent a reference pain quantification corresponding to the multiple pain intensities. A correspondence between the functional scores and the patient pain at different pain intensities may be specified and stored in the device memory 230.

The calibration circuit 460A-B may each compare the signal metrics 464 generated from the physiological or functional signals to the reference pain quantification such as one or both of the pain scales 462 or the functional scores 463. FIG. 4A illustrates a block diagram of the calibration circuit 460A that includes a correlator 465 that may calculate a correlation between the signal metrics 464 corresponding to n pain intensities (P1, P2, . . . , Pn), and the pain scale 462 corresponding to the same n pain intensities (P1, P2, . . . , Pn). For example, for signal metric p (1≤p≤m), the correlation may be represented by con {(X1(p), X2(p), . . . , Xn(p)), (rP1, rP2, . . . , rPn)}. Additionally or alternatively, the correlator 465 may calculate a correlation between the signal metrics 464 and the functional scores 463 each corresponding to n pain intensities (P1, P2, . . . , Pn). For example, for signal metric p (1≤p≤m), the correlation may be represented by corr{(X1(p), X2(p), . . . , Xn(p)), (F1, F2, . . . , Fn)}. Because the functional scores (F1, F2, . . . , Fn) correlate to the patient perceived pain intensities, the correlation between the signal metrics 464 and the functional scores 462 indirectly indicate the correlations between the signal metrics 412 and the patient perceived pain intensities. It is recognized that in some patients such as those with speech or mental disorders, acquiring patient subjective pain description or patient self-reported pain scales 462 may not be feasible. The correlations between the signal metrics 464 and the patient self-reported pain scales 462, corr{(X1(p), X2(p), . . . , Xn(p)), (rP1, rP2, . . . , rPn)}, may be more likely subject to inter- or intra-patient variation and therefore not reliable. Comparatively, the correlations between the signal metrics 464 and the functional scores 463, corr{(X1(p), X2(p), Xn(p)), (F1, F2, . . . , Fn)}, may be a more feasible measure in these patients for establishing or updating the fusion model.

In some examples, the correlator 465 may perform regression analysis and determine a regression line or curve that fits the data. The slope or trend of the fitted line or curve may indicate the sensitivity of the signal metric to pain. The fusion model generator 322 may generate or update the fusion model, such as by assigning weight factors for the signal metrics, based on the calculated correlation. In an example, the weight factors may be proportional to the correlations.

In some examples, the correlator 465 may use both the correlation between the signal metrics 464 and the pain scale 462, and the correlation between the signal metrics 464 and the functional scores 463, to determine or adjust the fusion model. In an example, between two signal metrics X(a) and X(b) that correlate almost equally well with the patient self-reported pain scales 462, if the functional scores 463 correlates with X(a) more closely than with X(b), then the fusion model may include a greater weight factor for X(a) that a weight factor for X(b).

FIG. 4B illustrates a block diagram of the calibration circuit 460B that includes a reference pain curve generator 466, a psychometric curve generator 467, and a comparator 468. The reference pain curve generator 466, which receives reference pain 461 such as the pain scales 462 or the functional scores 462 as input, may generate a reference pain curve that represents patient-reported pain intensities or functional scores at various pain intensities. The psychometric curve generator 467 may receive signal metrics 464 as input and generate one or more psychometric curves {Cx(1), Cx(2), . . . , Cx(m)} corresponding to the respective m signal metrics. The psychometric curves represent patient physiological or functional responses (as indicated by the respective signal metrics) at various pain intensities. In various examples, the reference pain curve generator 466 and the psychometric curve generator 467 may each perform curve smoothing, regression, interpolation, or extrapolation, among other curve fitting procedures. The reference pain curve and the one or more psychometric curves {Cx(1), Cx(2), . . . , Cx(m)} may be graphically displayed on a screen such as on the output unit 242. Examples of the reference pain curve and psychometric curves corresponding to various pain intensities are discussed below, such as with reference to FIG. 5.

The comparator 468 may compare the reference pain curve and each of the psychometric curves to determine an alignment metric indicating morphological similarity between the reference pain curve and each of the psychometric curves. Examples of the alignment metric may include multi-dimensional distance measures such as a mean-squared error, distance in a normed vector space (such as L1 norm, L2 norm or Euclidian distance, and infinite norm), correlation coefficient, mutual information, or ratio image uniformity, among others. The fusion model generator 322 may use the alignment metric to establish or adjust the fusion model. In an example, the fusion model generator 322 may determine weight factors for the signal metrics to be proportional to the alignment metrics between the pain perception curve and the generated psychometric curves.

Figure 5:
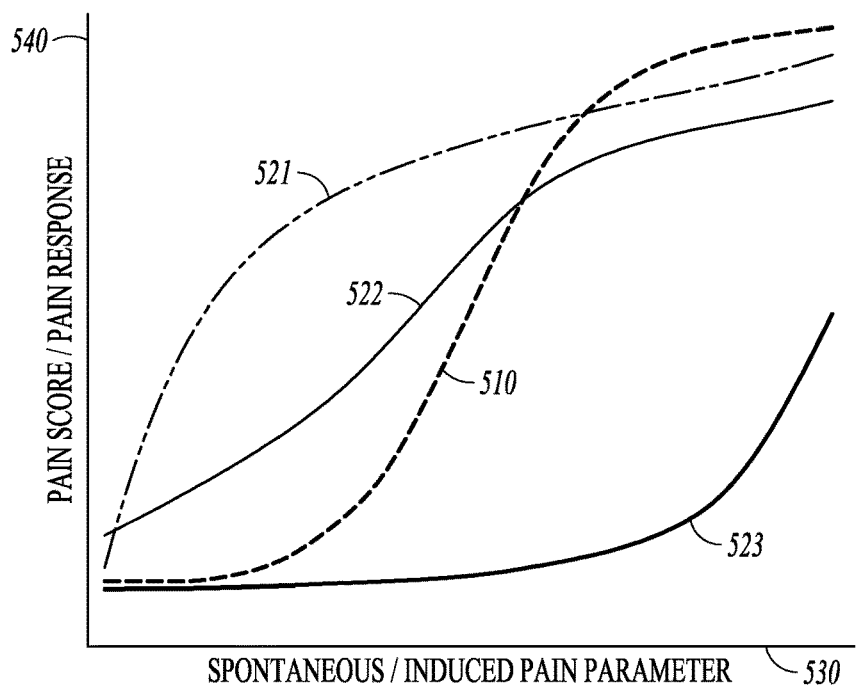
FIG. 5 illustrates, by way of example and not limitation, a reference pain curve and three psychometric curves generated during a pain assessment session.

FIG. 5 illustrates, by way of example and not limitation, a reference pain curve 510 and three psychometric curves 521-523, which may be respectively generated by the pain perception cure generator 466 and the psychometric curve generator 467 of the calibration circuit 460B. The horizontal axis 530 represents various pain intensities, such as energy levels of a pain-induction stimulation or dosage of pain-induction agents applied in a pain assessment session, or various pain intensities corresponding to spontaneous pain episodes. The vertical axis 540 represents reference pain or patient physiological or functional responses to pain. The reference pain curve 510 depicts patient-reported pain intensities or functional scores varying with various pain intensities. The psychometric curves 521-523 depict measurements of respective signal metrics corresponding to various pain intensities. In the example as illustrated in FIG. 5, the reference pain curve 510 has an "S" shape, indicating the patient self-reported pain perception or the functional score is a sigmoid-type of function of the intensities of spontaneous or induced pain episodes. Among the illustrative psychometric curves 521-523, the curve 522 has a similar "S" shape comprising both a concave and a convex portion within the range of the pain intensity parameter tested and displayed (as shown in the horizontal axis 530). The psychometric curve 521 has a convex shape, and the psychometric curve 523 has a concave shape, neither of which is similar to the "S"-shaped reference pain curve 510. The comparator 468 may compute alignment metrics, such as Euclidean distances, between the reference pain curve 510 and each of the psychometric curves 521-523. The psychometric curve 522 is morphologically more aligned with the reference pain curve 510. The fusion model generator may accordingly generate or adjust a fusion model such as by assigning a larger weight factor to the signal metric associated with the psychometric curve 522, than to the signal metrics associated with the psychometric curves 521 or 523.

Figure 6:
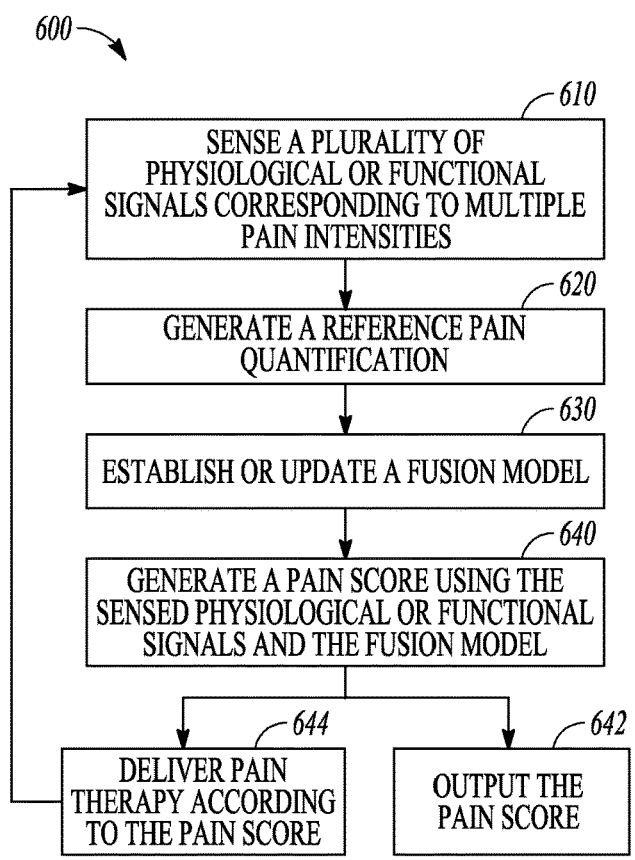
FIG. 6 illustrates, by way of example and not limitation, a flow chart of a method for managing pain in a patient.

FIG. 6 illustrates, by way of example and not limitation, a method 600 for managing pain in a patient. The method 600 may be implemented in a medical system, such as the pain management system 200 or 300. In an example, at least a portion of the method 600 may be executed by a neuromodulator device (IND) such as the implantable neuromodulator 310. In an example, at least a portion of the method 600 may be executed by an external programmer or remote server-based patient management system, such as the external system 320 communicatively coupled to the IND 310. The method 600 may be used to provide neuromodulation therapy to treat chronic pain or other disorders.

The method 600 begins at step 610, where a plurality of physiological or functional signals may be sensed such as via electrodes or ambulatory sensors associated with the patient. Examples of the physiological signals may include cardiac, pulmonary, or neural signals, such as, by way of example of limitation, electrocardiograph (ECG) or intracardiac electrogram, heart rate signal, heart rate variability signal, cardiovascular pressure signal, or heart sounds signal, respiratory signal, a thoracic impedance signal, or a respiratory sounds signal, or neural activity signal. The physiological signals may also include blood chemistry measurements or biomarkers that are indicative of onset, intensity, severity, duration, or different patterns of pain. In some examples, more functional signals may additionally be sensed at 610. Examples of the functional signals may include, for example, patient posture, gait, balance, or physical activity signals, among others. The functional signals may responsively co-variate with a pain episode.

At 620, a reference pain quantification corresponding to multiple pain intensities may be generated. The reference pain quantification may be generated during spontaneous pain episodes occurred in an ambulatory setting in patient daily life, or generated during induced pain episodes when a clinician executes a pain assessment session in a clinic. The spontaneous pain episodes may trigger recording of a plurality of physiological or functional signals, automatically or activated at least partially by the patient. The induction of pain episodes with various pain intensities may be generated by executing a pain assessment protocol, which may include electrostimulation or a stress test to induce paint with various pain intensities.

At 630, a fusion model may be established or updated. The fusion model may be used to algorithmically combine the sensed physiological or functional signals to determine an objective pain score. The fusion model may be established or calibrated based on measurements from the plurality of physiological or functional signals and the reference pain quantification corresponding to multiple pain intensities. During the spontaneous or induced pain episode, one or more physiological or functional signals may be sensed, and a plurality of signal metrics may be generated from the sensed physiological or functional signals, such as via the signal metrics generator 221. The signal metrics may include statistical parameters, morphological parameters, or temporal parameters. The fusion model may involve instructions for combining the measurements of the signal metrics using a specific algorithm. Examples of the fusion algorithms may include weighted averages, voting, decision trees, or neural networks, among other linear or nonlinear algorithms. In an example, the fusion model may include weighted combination of the signal metrics weighted by their respective weight factors. The combination can be linear or nonlinear.

For multiple spontaneous or induced pain episodes with multiple pain intensities, a set of signal metrics may be measured corresponding to each of the plurality of pain intensities. Also during the spontaneous or induced pain episode, reference pain quantification may also be generated. The physiological or functional signal metrics may be compared to the reference pain quantification, such as one or both of the pain scales and the functional scores during spontaneous or induced pain episodes, and determine or update the structure or one or more parameters of the fusion model based on the comparison. Examples of the fusion model establishment or update are discussed below such as with reference to FIG. 7.

At 640, a pain score may be generated using the measurements of the signal metrics and the fusion model. The pain score may be represented as a numerical or categorical value that quantifies overall pain quality in the subject. In an example, the fusion model includes a weighted combination of signal metrics. A composite signal metric may be generated using a combination of the signal metrics weighted by their respective weight factors. The composite signal metric may be categorized as one of a number of degrees of pain by comparing the composite signal metric to one or more threshold values or range values, and a corresponding pain score may be assigned based on the comparison. In another example, the signal metrics may be compared to their respective threshold values or range values and a corresponding signal metric-specific pain score may be determined. A composite pain score may be generated using a linear or nonlinear fusion of the signal metric-specific pain scores each weighted by their respective weight factors.

At 642, the pain score may be output to a user or to a process, such as via the output unit 242 as illustrated in FIG. 2. The pain score, including the composite pain score and optionally together with metric-specific pain scores, may be displayed on a display screen. Other information such as the physiological or functional signals and the signal metrics may also be output for display or for further processing. In some examples, alerts, alarms, emergency calls, or other forms of warnings may be generated to signal the system user about occurrence of a pain episode or aggravation of pain as indicated by the pain score.

The method 600 may include, at 644, an additional step of delivering a pain therapy to the patient according to the pain score. The pain therapy may include electrostimulation therapy, such as spinal cord stimulation (SCS) via electrodes electrically coupled to the electrostimulator. The SCS may be in a form of stimulation pulses that are characterized by pulse amplitude, pulse width, stimulation frequency, duration, on-off cycle, waveform, among other stimulation parameters. Other electrostimulation therapy, such as one or a combination of DBS, FES, VNS, TNS, or PNS at various locations, may be delivered for pain management. The pain therapy may additionally or alternatively include a drug therapy such as delivered by using an intrathecal drug delivery pump.

In various examples, the pain therapy (such as in the form of electrostimulation or drug therapy) may be delivered in a closed-loop fashion. Therapy parameters, such as stimulation waveform parameters, stimulation electrode combination and fractionalization, drug dosage, may be adaptively adjusted based at least on the pain score. The pain-relief effect of the delivered pain therapy may be assessed based on the signal metrics such as the cardiovascular parameters, and the therapy may be adjusted to achieve desirable pain relief. The therapy adjustment may be executed continuously, periodically at specific time, duration, or frequency, or in a commanded mode upon receiving from a system user a command or confirmation of parameter adjustment. In an example, if the pain score exceeds the pain threshold (or falls within a specific range indicating an elevated pain), then the first electrostimulation may be delivered. Conversely, if the composite pain score falls below a respective threshold value (or falls within a specific range indicating no pain or mild pain), then a second pain therapy, such as second electrostimulation may be delivered. The first and second electrostimulations may differ in at least one of the stimulation energy, pulse amplitude, pulse width, stimulation frequency, duration, on-off cycle, pulse shape or waveform, electrostimulation pattern such as electrode configuration or energy fractionalization among active electrodes, among other stimulation parameters. The method 600 may proceed at 610 to sense physiological or functional signals in response to the therapy delivered at 644. In some examples, the responses of the signal metrics to pain therapy delivered at 644 may be used to adjust the fusion model such as by adjusting the weight factors for the signal metrics.

Figure 7:
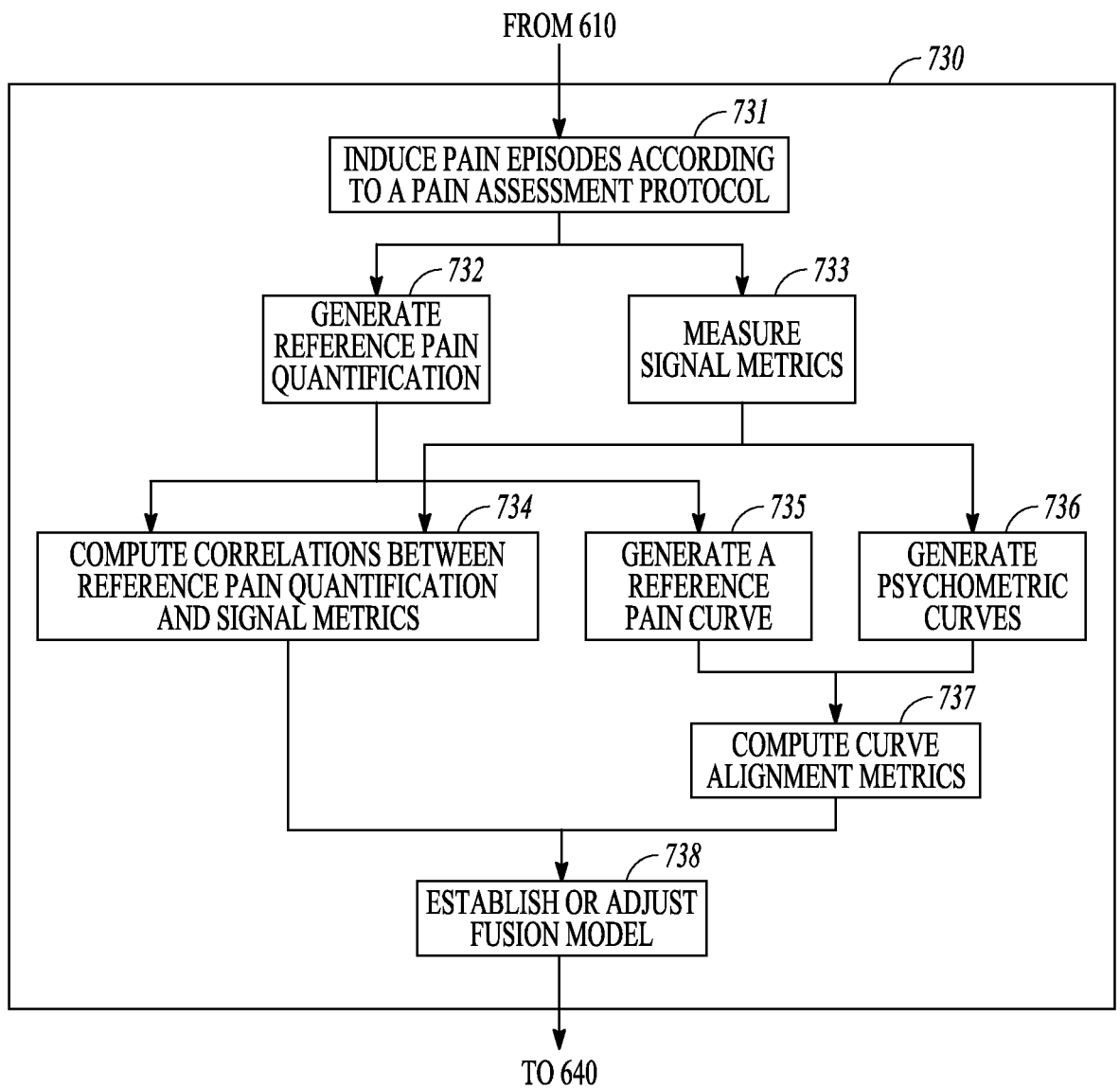
FIG. 7 illustrates, by way of example of not limitation, a flow chart of a method for establishing or updating a fusion model.

FIG. 7 illustrates, by way of example of not limitation, a diagram of a method 730 for establishing or updating a fusion model using a plurality of physiological or functional signals and a reference pain quantification corresponding to the multiple pain intensities. The method 730 may be an embodiment of the steps of generating the reference pain quantification 620 and establishing or updating the fusion model 630 as illustrated in method 600.

The method 730 begins at 731 with inducing pain episodes. The pain induction may involve delivering different levels of stimulation energy according to a pain assessment protocol via an external stimulator or the implantable neuromodulator 310 to induce pain. The pain assessment protocol may include electrostimulation with different levels of stimulation energy, which may result in different pain intensities. In an example, the pain assessment protocol may include trains of electrostimulation at different levels of stimulation energy for pain therapy, such as during a patient follow-up visit in a clinic. The different stimulation energy may be achieved by adjusting the pulse intensity, duration, frequency, on/off period, or electrode selection and stimulation vector configuration, among other therapy parameters. In an example, the pain assessment session may include a low stimulation energy level such as by temporarily withholding delivery of pain-relief electrostimulation, a high stimulation energy level such as by delivering the maximal tolerable and safe pain-relief stimulation as prescribed by the clinician, and optionally one or more intermediate stimulation energy levels between the minimal and maximal energy levels to achieve intermediate levels of pain reduction effect. A patient with chronic pain may experience various degrees of pain symptoms corresponding to the stimulation energy levels. The pain assessment protocol may include respective durations for each stimulation energy level, such as to allow patient adaptation to changes of stimulation energy from one level to another, and to allow stabilization of patient physiological or functional responses and pain sensation. The stimulation energy levels may be arranged in a ramp-up, a ramp-down, an intermittent, or a random order. The pain assessment protocol may additionally or alternatively involve pressure, thermal, or other peripheral somatosensory stimulations, a stress test, or other non-pain related tasks.

At 732, a reference pain quantification may be generated. The reference pain quantification may be generated during the pain episodes using the calibration circuit 460A or 460B as illustrated in FIGS. 4A-B. In an example, the reference pain quantification may include patient self-reported perceived pain scales corresponding to the multiple pain intensities during the spontaneous or induced pain episodes. The patient self-reported perceived pain scales may take numerical or categorical values. In some examples, the user input may include patient qualitative pain description such as a pain drawing or a patient questionnaire. The qualitative pain description may be transformed to pain scales, such as a discrete or continuous numeric value. In another example, the reference pain quantification may include functional scores corresponding to the multiple pain intensities during the spontaneous or induced pain episodes. The functional scores represent patient motion control functionality such as a posture, a gait, a balance while in locomotion, a locomotion pattern, or a physical activity level. The patient may undergo a standard functional assessment test, such as one or more of a gait analysis procedure, a six-minute walk test, or a timed up-and-go test, among other standardized tests, and functional scores may be obtained from the standardized tests. The functional scores indicative various levels of pain intensities. The patient with chronic pain may present with significantly unbalanced posture and abnormal gait or locomotion patterns, shorter six-minute walk distance, or longer time for completion of the timed up-and-go test.

At 733, a plurality of signal metrics may be measured during the induced pain episodes. The signal metrics may be generated from physiological or functional signals that are sensed during the induced pain episodes. At 734, correlations between the reference pain quantification and the signal metrics corresponding to various pain intensities may be computed, such as using the correlator 465. In an example, the correlations are evaluated between the signal metrics corresponding to multiple pain intensities and the patient self-reported pain scale corresponding to the same multiple pain intensities. In another example, the correlations are evaluated between the signal metrics corresponding to multiple pain intensities and the functional scores corresponding to the same multiple pain intensities. The signal metric measurements and the pain scales may be graphically presented to a system user such as to be displayed in the user interface 234. A regression analysis may be performed to determine a regression line or curve that fits the pain scales and the signal metric measurements during the induced pain episodes. The correlations may be graphically represented by the spreadness of the signal metric measurements with respect to the regression line. The slope or trend of the fitted line or curve may indicate the sensitivity of the signal metric to the pain. Then, at 738, a fusion model may be generated, or an existing fusion model may be updated, based on the calculated correlation. In an example, the fusion model may include a linear or a nonlinear combination of signal metrics weighted by their respective weight factors. The fusion model may be updated by assigning weight factors for the signal metrics based on the calculated correlation. In an example, the weight factor for a signal metric is proportional to the correlation between the reference pain quantification and the signal metric.

In addition to or in lieu of establishing or updating the fusion model based on the correlations between reference pain quantification and signal metrics such as obtained at 734, the fusion model may be established or updated based on similarity between patient pain perception and physiological or functional response to pain. As illustrated in FIG. 7, at 735 a reference pain curve may be generated, such as using the reference pain curve generator 466. The reference pain curve, such as the curve 510 in FIG. 5, represents patient-reported pain intensities, or functional scores, at various pain intensities. At 736, one or more psychometric curves may be generated for the respective signal metrics. The psychometric curves, such as the curve 521-523 in FIG. 5, represent patient physiological or functional responses (as indicated by the respective signal metrics) at various pain intensities. The reference pain curve and the one or more psychometric curves may each be processed including curve smoothing, regression, interpolation, or extrapolation. At 737, an alignment metric between the reference pain curve and each of the psychometric curves may be computed. The alignment metric indicates a degree of morphological similarity between the reference pain curve and each of the psychometric curves. The alignment metric may be computed as a multi-dimensional distance measures such as a mean-squared error, distance in a normed vector space, correlation coefficient, mutual information, or ratio image uniformity, among others. Then, at 738, a fusion model may be generated, or an existing fusion model may be updated, based on the curve alignment metric. In an example, the fusion model may include weighted combination of the signal metrics weighted by their respective weight factors. The fusion model may be updated by assigning weight factors for the signal metrics based on the respective alignment metrics. In an example, the weight factors for a signal metric is proportional to the alignment metric between the reference pain curve and the psychometric curve corresponding to the signal metric.

Figure 8:
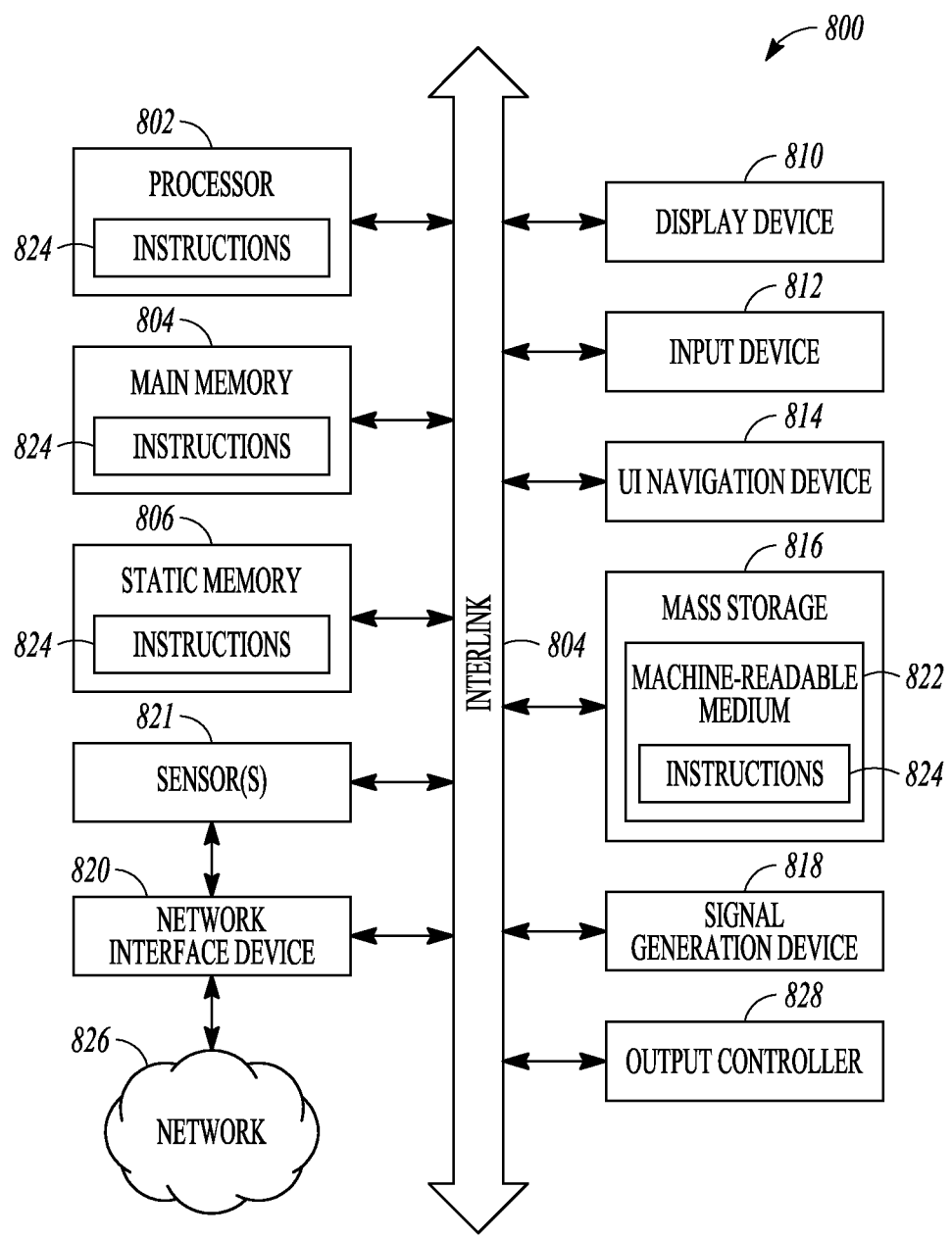
FIG. 8 illustrates, by way of example of not limitation, a block diagram of an example machine upon which any one or more of the techniques discussed herein may perform.

FIG. 8 illustrates generally a block diagram of an example machine 800 upon which any one or more of the techniques (e.g., methodologies) discussed herein may perform. Portions of this description may apply to the computing framework of various portions of the LCP device, the IND, or the external programmer.

In alternative embodiments, the machine 800 may operate as a standalone device or may be connected (e.g., networked) to other machines. In a networked deployment, the machine 800 may operate in the capacity of a server machine, a client machine, or both in server-client network environments. In an example, the machine 800 may act as a peer machine in peer-to-peer (P2P) (or other distributed) network environment. The machine 800 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 800 may include a hardware processor 802 (e.g., a central processing unit (CPU), a graphics processing unit (GPU), a hardware processor core, or any combination thereof), a main memory 804 and a static memory 806, some or all of which may communicate with each other via an interlink (e.g., bus) 808. The machine 800 may further include a display unit 810 (e.g., a raster display, vector display, holographic display, etc.), an alphanumeric input device 812 (e.g., a keyboard), and a user interface (UI) navigation device 814 (e.g., a mouse). In an example, the display unit 810, input device 812 and UI navigation device 814 may be a touch screen display. The machine 800 may additionally include a storage device (e.g., drive unit) 816, a signal generation device 818 (e.g., a speaker), a network interface device 820, and one or more sensors 821, such as a global positioning system (GPS) sensor, compass, accelerometer, or other sensor. The machine 800 may include an output controller 828, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 816 may include a machine readable medium 822 on which is stored one or more sets of data structures or instructions 824 (e.g., software) embodying or utilized by any one or more of the techniques or functions described herein. The instructions 824 may also reside, completely or at least partially, within the main memory 804, within static memory 806, or within the hardware processor 802 during execution thereof by the machine 800. In an example, one or any combination of the hardware processor 802, the main memory 804, the static memory 806, or the storage device 816 may constitute machine readable media.

While the machine readable medium 822 is illustrated as a single medium, the term "machine readable medium" may include a single medium or multiple media (e.g., a centralized or distributed database, and/or associated caches and servers) configured to store the one or more instructions 824.

The term "machine readable medium" may include any medium that is capable of storing, encoding, or carrying instructions for execution by the machine 800 and that cause the machine 800 to perform any one or more of the techniques of the present disclosure, or that is capable of storing, encoding or carrying data structures used by or associated with such instructions. Non-limiting machine readable medium examples may include solid-state memories, and optical and magnetic media. In an example, a massed machine readable medium comprises a machine readable medium with a plurality of particles having invariant (e.g., rest) mass. Accordingly, massed machine-readable media are not transitory propagating signals. Specific examples of massed machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 824 may further be transmitted or received over a communications network 826 using a transmission medium via the network interface device 820 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 820 may include one or more physical jacks (e.g., Ethernet, coaxial, or phone jacks) or one or more antennas to connect to the communications network 826. In an example, the network interface device 820 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 800, and includes digital or analog communications signals or other intangible medium to facilitate communication of such software.

Various embodiments are illustrated in the figures above. One or more features from one or more of these embodiments may be combined to form other embodiments.

The method examples described herein can be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A system, comprising:
   a sensor circuit coupled to one or more sensors configured to sense from a patient a plurality of physiological or functional signals;
   a controller circuit configured to:
   calculate a pain score using a fusion model that algorithmically combines the sensed plurality of physiological or functional signals using a weighted combination or a neural network;
   receive a user input via a user interface about pain perception of the patient; and
   adjust the fusion model by updating a parameter value or a structure of the fusion model based at least in part on the received user input, and calibrate the pain score using the adjusted fusion model; and
   an output unit configured to provide the calibrated pain score to a user or a process.

2. The system of claim 1, wherein the controller circuit is configured to:
   calculate the pain score using a combination of signal metrics of the sensed plurality of physiological or functional signals each weighted by respective weight factors; and
   calibrate the pain score by updating one or more of the weight factors based on the received user input.

3. The system of claim 2, wherein:
   the user input about pain perception includes a plurality of pain scales; and
   updating the one or more weight factors is proportional to correlations between (i) values of respective signal metrics corresponding to the plurality of pain scales and (ii) the plurality of pain scales.

4. The system of claim 2, wherein:
   the user input includes a pain perception curve; and
   updating the one or more weight factors is proportional to an alignment between (i) the pain perception curve and (ii) psychometric curves each representing values of a signal metric at respective pain scales.

5. The system of claim 1, comprising:
   a pain management device that includes the sensor circuit and the controller circuit; and
   a mobile device operably in communication with the pain management device, the mobile device including the user interface to receive the user input about pain perception.

6. The system of claim 1, wherein the user input further includes a context of the pain perception including a physical state or activity of the patient.

7. The system of claim 1, comprising a therapy unit configured to provide or adjust a neuromodulation therapy or a drug therapy in accordance with the calibrated pain score.

8. The system of claim 1, wherein the output unit is configured to generate a recommendation to the user to initiate or adjust a pain therapy based on the calibrated pain score.

9. The system of claim 1, wherein the output unit is configured to generate an alert of an adverse event or a therapy effect based on the calibrated pain score.

10. A system comprising:
a sensor circuit coupled to one or more sensors configured to sense a plurality of physiological or functional signals from a patient; and
a controller circuit, configured to, in response to a treatment provided to the patient;
quantify a patient response to the treatment using a fusion model that algorithmically combines the sensed plurality of physiological or functional signals using a weighted combination or a neural network;
receive a user feedback on the treatment;
adjust the fusion model by updating a parameter value or a structure of the fusion model based at least in part on the received user feedback, and calibrating the quantified patient response using the adjusted fusion model; and
generate a control signal to adjust the treatment based on the calibrated quantified patient response.

11. The system of claim 10, wherein the treatment includes a pain therapy, and the user feedback includes a pain perception and a context thereof including a physical state or activity of the patient.

12. The system of claim 10, wherein the treatment includes a neuromodulation therapy or a drug therapy, and wherein to adjust the treatment includes to adjust a neuromodulation parameter or a drug dosage in accordance with the calibrated quantified patient response.

13. The system of claim 10, comprising an output unit configured to generate a recommendation to a user to adjust the treatment based on the calibrated quantified patient response.

14. A method comprising:
sensing a plurality of physiological or functional signals from a patient using one or more sensors;
calculating, via a controller circuit, a pain score using a fusion model that algorithmically combines the sensed plurality of physiological or functional signals using a weighted combination or a neural network;
via the controller circuit, adjusting the fusion model by updating a parameter value or a structure of the fusion model based at least in part on a user input about pain perception of the patient provided via a user interface, and calibrating the pain score using the adjusted fusion model; and
outputting the calibrated pain score to a user or a process.

15. The method of claim 14, wherein:
calculating the pain score is by using a combination of signal metrics of the sensed plurality of physiological or functional signals each weighted with respective weight factors; and
calibrating the pain score includes updating one or more of the weight factors based on the user input.

16. The method of claim 15, wherein the user input about pain perception includes a plurality of pain scales, and updating the one or more weight factors is proportional to correlations between (i) values of respective signal metrics corresponding to the plurality of pain scales and (ii) the plurality of pain scales.

17. The method of claim 15, wherein the user input includes a pain perception curve, and updating the one or more weight factors is proportional to an alignment between (i) the pain perception curve and (ii) psychometric curves each representing values of a signal metric at respective pain scales.

18. The method of claim 14, wherein the user input includes a patient feedback to a pain therapy.

19. The method of claim 14, further comprising generating a recommendation to the user to initiate or adjust a pain therapy.

20. The method of claim 14, further comprising adjusting, via the controller circuit, a neuromodulation parameter or a drug dosage in accordance with the calibrated pain score.

* * * * *